United States Patent
Barnea et al.

(10) Patent No.: US 10,619,155 B2
(45) Date of Patent: Apr. 14, 2020

(54) METHODS FOR LABELING AND MANIPULATING A CELLULAR CIRCUIT

(71) Applicant: Brown University, Providence, RI (US)

(72) Inventors: Gilad Barnea, Providence, RI (US);
Mustafa Talay, Providence, RI (US);
Ethan Richman, Sharon, MA (US);
John Szymanski, New York, NY (US);
Mark Johnson, Boston, MA (US);
John Fisher, Providence, RI (US);
Nathaniel Snell, Providence, RI (US)

(73) Assignee: BROWN UNIVERSITY, Providence, RI (US)

( * ) Notice: Subject to any disclaimer, the term of this patent is extended or adjusted under 35 U.S.C. 154(b) by 0 days.

(21) Appl. No.: 15/558,900

(22) PCT Filed: Mar. 15, 2016

(86) PCT No.: PCT/US2016/022478
§ 371 (c)(1),
(2) Date: Sep. 15, 2017

(87) PCT Pub. No.: WO2016/149274
PCT Pub. Date: Sep. 22, 2016

(65) Prior Publication Data
US 2018/0066249 A1 Mar. 8, 2018

Related U.S. Application Data

(60) Provisional application No. 62/134,334, filed on Mar. 17, 2015.

(51) Int. Cl.
| | | |
|---|---|---|
| G01N 33/58 | (2006.01) | |
| C12N 15/10 | (2006.01) | |
| G01N 33/50 | (2006.01) | |
| C07K 14/605 | (2006.01) | |
| C07K 14/72 | (2006.01) | |

(52) U.S. Cl.
CPC ........ *C12N 15/1055* (2013.01); *C07K 14/605* (2013.01); *C07K 14/723* (2013.01); *G01N 33/5032* (2013.01); *G01N 33/5041* (2013.01); *G01N 33/5058* (2013.01); *G01N 33/58* (2013.01); *C07K 2319/035* (2013.01); *C07K 2319/50* (2013.01)

(58) Field of Classification Search
None
See application file for complete search history.

(56) References Cited

U.S. PATENT DOCUMENTS

| | | |
|---|---|---|
| 4,879,236 A | 11/1989 | Smith et al. |
| 5,871,986 A | 2/1999 | Boyce |
| 6,440,419 B1 * | 8/2002 | Hein ................. A61K 47/62 424/134.1 |
| 7,112,430 B2 * | 9/2006 | Madison ............. C12N 9/6424 435/226 |
| 2012/0077706 A1 * | 3/2012 | Lee .................. C12N 15/1055 506/11 |
| 2013/0317086 A1 * | 11/2013 | Guire .................. C12N 15/87 514/44 A |

OTHER PUBLICATIONS

Boucard et al in 'High Affinity Neurexin Binding to Cell Adhesion G-Protein Coupled Receptor CIRL1/Latrophilin1 Produces an Intercellular Adhesion Complex' (JBC Jan. 19, 2012, vol. 287, No. 12; pp. 1-29), (Year: 2012).*
Score result to Hein et al for U.S. Pat. No. 6,440,419 (Year: 2002).*
Boucard et al., "High affinity neurexin binding to cell adhesion G-protein-coupled receptor CIRL1/latrophilin-1 produces an intercellular adhesion complex," J Biol Chem. 287(12):9399-413 (29 pages) (2012).
International Search Report and Written Opinion for International Application No. PCT/US16/22478, dated Jun. 20, 2016 (18 pages).
Barnea et al., "The Genetic Design of Signaling Cascades to Record Receptor Activation", PNAS, vol. 105, No. 1, Jan. 8, 2008, pp. 64-69.
Giepmans et al., "The Fluorescent Toolbox for Assessing Protein Location and Function", Science, vol. 312, Issue 5771, Apr. 14, 2006, pp. 217-224.
Green et al., "Molecular Cloning: A Laboratory Manual", Cold Spring Harbor Laboratory Press, vol. 1, Fourth Edition, 2012, 34 pages.
Groth et al., "Construction of Transgenic *Drosophila* by Using the Site-Specific Integrase from Phage PhiC31", Genetics, vol. 166, Apr. 2004, pp. 1775-1782.
Markstein et al., "Exploiting Position Effects and the Gypsy Retrovirus Insulator to Engineer Precisely Expressed Transgenes", Nat. Genet., vol. 40, No. 4, Apr. 2008, pp. 476-483.
Shaner et al., "A Guide to Choosing Fluorescent Proteins", Nature Methods, vol. 2, No. 12, Dec. 2005, pp. 905-909.
Zhang et al., "Creating New Fluorescent Probes for Cell Biology", Nat. Rev. Mol. Cell Biol., vol. 3, Dec. 2002, pp. 906-918.

* cited by examiner

*Primary Examiner* — Catherine S Hibbert
(74) *Attorney, Agent, or Firm* — Adler Pollock & Sheehan P.C.

(57) ABSTRACT

The invention relates to methods and kits for labeling and manipulating a cellular circuit. The methods includes transfecting a first-order cell in the cellular circuit with a nucleic acid molecule encoding a tethered ligand, and a second-order cell in the cellular circuit with a nucleic acid molecule encoding a receptor and an effector fusion polypeptide, a nucleic acid molecule encoding a receptor interactor and protease fusion polypeptide, and a nucleic acid molecule encoding a reporter/modifier gene.

16 Claims, 5 Drawing Sheets

Specification includes a Sequence Listing.

SEQUENCE LISTING

```
<160> NUMBER OF SEQ ID NOS: 36

<210> SEQ ID NO 1
<211> LENGTH: 3130
<212> TYPE: DNA
<213> ORGANISM: Artificial Sequence
<220> FEATURE:
<223> OTHER INFORMATION: Synthetic Construct

<400> SEQUENCE: 1
tcggagtact gtcctccgag cggagtactg tcctccgagc ggagtactgt cctccgagcg      60
gagtactgtc ctccgagcgg agtactgtcc tccgagcgga gactctagcg agcgccggag     120
tataaataga ggcgcttcgt ctacggagcg acaattcaat tcaaacaagc aaagtgaaca     180
cgtcgctaag cgaaagctaa gcaaataaac aagcgcagct gaacaagcta aacaatctgc     240
agtaaagtgc aagttaaagt gaatcaatta aaagtaacca gcaaccaagt aaatcaactg     300
caactactga aatctgccaa gaagtaatta ttgaatacaa gaagagaact ctgaataggg     360
aattgggaat tcaaaatgag tgcacttctg atcctagccc ttgtgggagc tgctgttgct     420
cattcacagg gcacattcac cagtgactac agcaagtatc tggactccag gcgtgcccaa     480
gattttgtgc agtggttgat gaatacaggt accggcaacg gaaatgggaa cggtaatggc     540
accggtgagc aaaagctcat ttctgaagag gacttgggga acggaaatgg caatggtaac     600
gggaatggaa acggcaatgg taacgggaat actagtcaga catctgtgtc cccctcaaaa     660
```

```
gtcatcctgc cccggggagg ctccgtgctg gtgacatgca gcacctcctg tgaccagccc    720
aagttgttgg gcatagagac cccgttgcct aaaaaggagt tgctcctgcc tgggaacaac    780
cggaaggtgt atgaactgag caatgtgcaa gaagatagcc aaccaatgtg ctattcaaac    840
tgccctgatg ggcagtcaac agctaaaacc ttcctcaccg tgtactggac tccagaacgg    900
gtggaactgg cacccctccc ctcttggcag ccagtgggca agaaccttac cctacgctgc    960
caggtggagg tggggcacc ccgggccaac ctcaccgtgg tgctgctccg tggggagaag   1020
gagctgaaac gggagccagc tgtggggag cccgctgagg tcacgaccac ggtgctggtg   1080
aggagagatc accatggagc caatttctcg tgccgcactg aactggacct gcggccccaa   1140
gggctggagc tgtttgagaa cacctcggcc ccctaccagc tccagacctt tgtcctgcca   1200
gcgactcccc cacaacttgt cagccccggg gtcctagagg tggacacgca ggggaccgtg   1260
gtctgttccc tggacgggct gttcccagtc tcggaggccc aggtccacct ggcactgggg   1320
gaccagaggt tgaaccccac agtcacctat ggcaacgact ccttctcggc caaggcctca   1380
gtcagtgtga ccgcagagga cgagggcacc cagcggctga cgtgtgcagt aatactgggg   1440
aaccagagcc aggagacact gcagacagtg accatctaca gctttccggc gcccaacgtg   1500
attctgacga agccagaggt ctcagaaggg accgaggtga cagtgaagtg tgaggcccac   1560
cctagagcca aggtgacgct gaatggggtt ccagcccagc cactgggccc gagggcccag   1620
ctcctgctga aggccacccc agaggacaac gggcgcagct ctcctgctc tgcaaccctg   1680
gaggtggccg gccagcttat acacaagaac cagacccggg agcttcgtgt cctgtatggc   1740
ccccgactgg acgagaggga ttgtccggga aactggacgt ggccagaaaa ttcccagcag   1800
actccaatgt gccaggcttg ggggaaccca ttgcccgagc tcaagtgtct aaaggatggc   1860
actttcccac tgcccatcgg ggaatcagtg actgtcactc gagatcttga gggcacctac   1920
ctctgtcggg ccaggagcac tcaaggggag gtcacccgcg aggtgaccgt gaatgtgctc   1980
tcccccggt atgagataat cggcatagtg gcgggcatac tgatcgcagt ggtgctggtc   2040
atcctgctgg tcctgtggct caagtcgaat ggcgatcgtg gctacaagac ggagagcgag   2100
aaggcggccg cctacggttc ccacaatccg aatgctgcac tcctgggaaa tactagcacc   2160
aatggatcgt accaccagca gcggcagcac catatgcatg gtggcggagg cggtggaggt   2220
gcagggcaac agcagcatca tgcccaacag cagatgcaca atgggcacaa cggtaatgga   2280
aatggaggag gcggcggcgg tggcggcatg atgtccagcg gaagtgggtc acttggctat   2340
ggcagcgatg ggcgacccca gatggcgggc ctggtgcagc cgaaggccaa gaaacgcgac   2400
tccaaggacg tcaaggagtg gtatgtgtaa tctagaggat ctttgtgaag gaaccttact   2460
tctgtggtgt gacataattg gacaaactac ctacagagat ttaaagctct aaggtaaata   2520
taaaattttt aagtgtataa tgtgttaaac tactgattct aattgtttgt gtatttaga    2580
ttccaaccta tggaactgat gaatgggagc agtggtggaa tgcctttaat gaggaaaacc   2640
tgttttgctc agaagaaatg ccatctagtg atgatgaggc tactgctgac tctcaacatt   2700
ctactcctcc aaaaaagaag agaaaggtag aagaccccaa ggactttcct tcagaattgc   2760
taagttttt gagtcatgct gtgtttagta atagaactct tgcttgcttt gctatttaca   2820
ccacaaagga aaagctgca ctgctataca agaaaattat ggaaaatat ttgatgtata   2880
gtgccttgac tagagatcat aatcagccat accacatttg tagaggtttt acttgcttta   2940
aaaaacctcc cacacctccc cctgaacctg aaacataaaa tgaatgcaat tgttgttgtt   3000
aacttgttta ttgcagctta taatggttac aaataaagca atagcatcac aaatttcaca   3060
```

| | | |
|---|---|---|
| aataaagcat | tttttcact gcattctagt tgtggtttgt ccaaactcat caatgtatct | 3120 |
| tatcatgtct | | 3130 |

<210> SEQ ID NO 2
<211> LENGTH: 5166
<212> TYPE: DNA
<213> ORGANISM: Artificial Sequence
<220> FEATURE:
<223> OTHER INFORMATION: Synthetic Construct

<400> SEQUENCE: 2

| | | |
|---|---|---|
| atttcccacc | ccttggccat cggcacttgg aaatcgctaa ggaaaagctt ctcgctggaa | 60 |
| caccattcgc | tgctggccat ccaggcagct ttttccccaa atacacataa cagttaggaa | 120 |
| agctgcaagt | tttcgcagtt ggccaaaaac gtcgtaagtg aaaattttcc tggtgctgcg | 180 |
| taaaaaatt | cgtaaaatat tagttaagcc tggttttgt aaactcaagt tgcccgagca | 240 |
| aaagtaaagt | gattctgatc aaaagtgcta aaactgattg attaggaaaa cgaagatcaa | 300 |
| acgaaatgtc | aaccaaagtc agcgaaaacc cttgtcgtgc agaatttcat tgattttttc | 360 |
| ttctgagccc | acgttggcca gttgggcact tgaaattatt tttaaaacgt tttgcatttt | 420 |
| gaagacatct | taggtgcccc tggggtatg caacggaaat gaggaaggac atgcctcatg | 480 |
| gctgggcgtg | ttgctgccac ccaaatagtc ctcttacgtc ccaattagaa tcccatagct | 540 |
| gcccatttca | agcattaacc gatgtactaa aaatagttgc aactattttc gcactctatt | 600 |
| cagcagcagt | tccagcgctg agccagaaaa ttcctgcgaa aggctgtcgt ggcaagtgtt | 660 |
| acccgcacac | atacacatca tccagatcca gccaatcccc ccgtggagtg gagtgaattt | 720 |
| tcattgacga | cggggcgaaa aagctctggc ggaagagcga cagagagaga gagaaacaga | 780 |
| gagagagaga | gagaagcggc actgagagcg caaccctcta gaacgctagc agagctcgcc | 840 |
| cggggatcga | gcgcagcggt ataaaagggc gcggggtggc tgagagcatc agttgtgaat | 900 |
| gaatgttcga | gccgagcaga cgtgccgctg ccttcgttaa tatcctttga ataagccaac | 960 |
| tttgaatcac | aagacgcata ccaaacgcgg ccgcaaaatg ccccctgcc agccacagcg | 1020 |
| accccctgctg | ctgttgctgc tgctgctggc ctgccagcca caggtcccct ccgctcaggt | 1080 |
| gatggacttc | ctgtttgaga agtggaagct ctacggtgac cagtgtcacc acaacctgag | 1140 |
| cctgctgccc | cctcccacgg agctggtgtg caacagaacc ttcgacaagt attcctgctg | 1200 |
| gccggacacc | cccgccaata ccacggccaa catctcctgc ccctggtacc tgccttggca | 1260 |
| ccacaaagtg | caacaccgct tcgtgttcaa gagatgcggg cccgacggtc agtgggtgcg | 1320 |
| tggaccccgg | gggcagcctt ggcgtgatgc ctcccagtgc cagatggatg gcgaggagat | 1380 |
| tgaggtccag | aaggaggtgg ccaagatgta cagcagcttc caggtgatgt acacagtggg | 1440 |
| ctacagcctg | tccctggggg ccctgctcct cgccttggcc atcctggggg gcctcagcaa | 1500 |
| gctgcactgc | acccgcaatg ccatccacgc gaatctgttt gcgtccttcg tgctgaaagc | 1560 |
| cagctccgtg | ctggtcattg atgggctgct caggacccgc tacagccaga aaattggcga | 1620 |
| cgacctcagt | gtcagcacct ggctcagtga tggagcggtg gctggctgcc gtgtggccgc | 1680 |
| ggtgttcatg | caatatggca tcgtggccaa ctactgctgg ctgctggtgg agggcctgta | 1740 |
| cctgcacaac | ctgctgggcc tggccaccct ccccgagagg agcttcttca gcctctacct | 1800 |
| gggcatcggc | tggggtgccc ccatgctgtt cgtcgtcccc tgggcagtgg tcaagtgtct | 1860 |
| gttcgagaac | gtccagtgct ggaccagcaa tgacaacatg ggcttctggt ggatcttgcg | 1920 |

```
gttccccgtc ttcctggcca tcctgatcaa cttcttcatc ttcgtccgca tcgttcagct    1980
gctcgtggcc aagctgcggg cacggcagat gcaccacaca gactacaagt tccggctggc    2040
caagtccacg ctgaccctca tccctctgct gggcgtccac gaagtggtct ttgccttcgt    2100
gacggacgag cacgcccagg gcaccctgcg ctccgccaag ctcttcttcg acctcttcct    2160
cagctccttc cagggcctgc tggtggctgt cctctactgc ttcctcaaca aggaggtgca    2220
gtcggagctg cggcggcgtt ggcaccgctg gcgcctgggc aaagtgctat gggaggagcg    2280
gaacaccagc aaccacaggg cctcatcttc gcccggccac ggccctccca gcaaggagct    2340
gcagtttggg aggggtggtg gcagccagga ttcatctgcg gagacccct tggctggtgg    2400
cctccctaga ttggctgaga gccccttcgg atccgagaac ctgtacttcc agagcccgcc    2460
taaacgcaag acactcaatg ccgctgccga agccaatgcc cacgctgatg gccatgctga    2520
tggcaatgct gatggtcatg tcgctaacac tgcagcaagc agcaacaacg cccgttttgc    2580
ggacttgacc aacattgaca cacccggcct cggccctacc acgacgacgt tacttgtcga    2640
gcccgctcgt tcgaaacgcc agagagtctc gagggcctgt gatcagtgtc gagctgcacg    2700
tgaaaagtgt gatggaatcc agccggcttg cttccctgt gtgtcgcagg gccggtcgtg    2760
tacctaccag gccagtccca agaagcgagg agtccgacg ggctacatcc gcactctcga    2820
actggctctg gcttggatgt tcgagaacgt tgcccgcagc gaggacgccc tccacaatct    2880
tttggtccgt gatgctggcc agggcagcgc tctcctggtc ggcaaagact cgcctgctgc    2940
agaacgcctg catgcaagat gggcgacgag tcgagtcaac aaaagcatca cccgtcttct    3000
ctcaggtcag gccgcacaag atccatctga agacggccaa tccccgtccg aagacataaa    3060
tgtccaagat gccggggcaa agacatccga cttccctcat gcgcctcact tgactttctc    3120
ggcgcctaag tctagtacag ctgagacacg cactctacca ggcccggtcc gaccacctat    3180
ttcggcaaac accctggaaa acaaccttca gccagatggt accgggatag ggaagctacc    3240
acccaatcat tggcgcctgc tggatatcta cttttcctac acgcattctt ggctccctat    3300
cctcgagaag aaagacatgt accaagcatt gtaccagtac tctgaacaag ctcgttgct    3360
tccctctgcg aatgtcgagt ctggcgttca tgccagctc tggagcgcgc tcgccctggc    3420
gtccttccag gctgctgcta ctgctgcatc gagtgctacg ggtccagctt cagctgctca    3480
tggccatgac aatgccatca atccttcacc tgcagacata tctgacacag cccgaaagct    3540
catacctttg gaaagcgggc cgttccaggt tcagcactgc agagcgttgc tgcttctttg    3600
tctcgtaagc cttgggcggg atgattggga gtctgcttgg ttgctggttg ctttgcggt    3660
ccgcgtccta cttgttgttc gcacccagtt gcctcctgat gatgaccggc cacgaccaag    3720
aatgcgtgcg ctgctcgtcg cgtgcttcat cgtggatacc attgtgtcta tgagacacaa    3780
cgtgccggcc catctcaagc cagacgacat tgcggatctg ccgttacctg aagacggtca    3840
agatcaatgg gagccgtgga caccatgtga gggcttaggc ggtgaacaca ccatgctgca    3900
aatgttgagg aacccggcat acccttaag cacattcaac cacctatatg gcgtgaccaa    3960
gctggttgct ttggagcttc tgccaagaat acgaacatct tcacagaacg ctcccttgga    4020
gttcaggtcg cggttgcagc aggtaatcgg ccacaattct ccttcagcg tctttgtcct    4080
ttcccaggat acagcatcgg cttttgtgcc tactgcatac cttacccgta ccgtttattt    4140
atgggcagct gccttttctg agcctctcaa cgaacactac tcgcatcttc tgatcgaaac    4200
tcttgatcag tatcagaagc ggtttggtac atatgcaatc ccacctctga tcccttctct    4260
tctagactcc cttcttgctt taaagaaaca atcacattct tcagagcggc atcgaaggca    4320
```

```
cttggaagag cttttccccg cctactcctc catttggcct cggggaggcc gacacagcaa    4380
tactggcctc caacccatac gacaacttga gcttccgccg actgcgactg ccactgcaag    4440
tatcatgccc catgtcatgg aacagcccct gtcaacgtca ataaatccgg tcaatgatcg    4500
gtttaatgga ataccgaatc ctacccccta caatagcgat gcggccctag acgcaattac    4560
tcaaaccaat gactacggat cagtcaatac ccatggcatt ctcagtacat atccaccacc    4620
tgccacccac ttgaacgagg cctcggtggc ccttgcgcct ggaggtgctc ctcccagacc    4680 accccgcca tacgttgata gtacaacgaa ccatcctcct taccatagta acctcgtccc    4740
catggccaat ttcggatatt cgactgtaga ctatgatgcg atggtggatg atctggcatc    4800
gatcgagtac acggatgcgg ttgacgttga tccgcagttc atgacgaacc tcgggtttgt    4860
cccagggtgt aattttagcg atatcaacac gtatgagcaa taggacgtct atcgataccg    4920
tcgactaaag ccaaatagaa aattattcag ttcctggctt aagttttaa aagtgatatt    4980 atttatttgg ttgtaaccaa ccaaaagaat gtaaataact aatacataat tatgttagtt    5040
ttaagttagc aacaaattga ttttagctat attagctact tggttaataa atagaatata    5100
tttatttaaa gataattgcg ttttattgt cagggagtga gtttgcttaa aaactcgttt    5160
agatcc                                                              5166

<210> SEQ ID NO 3
<211> LENGTH: 6266
<212> TYPE: DNA
<213> ORGANISM: Artificial Sequence
<220> FEATURE:
<223> OTHER INFORMATION: Synthetic Construct

<400> SEQUENCE: 3
cccggatcca gtcgagggat cactgaacta aaaagtaaag agaggagaaa caggagaagc      60
ccttaaagtg cgagttcgct ggagtgccta tcgatccttg agggcagcgc tcgatcctta     120
ttactattgg caggatcatt ttatacccct tacataaaaa tatcagtatc agtttgttcc     180
cttatcatgc gtgctctttg acatatccgg gaatttattt ctattttgc ttagtcaaac     240 tgaagaccat tttgtcccaa cataaaatat gtaaatatt ttttttatc attttaaatt     300 ctcagggatt aagtcaatgt ttgaaaactt ctagctgact tgcgctccac taccactcgg    360
catgcgtgcc cctgattagt aggccaggtg gtgggccttt ggcacgatcg caaccctaag    420
gactgcaacc gaatagcatt gagaaggaga ccaggatttc tgcactcaaa ggtgaaattg    480
tctgagcacg gaacacggaa aaacaacaac aaaacatgg cagacggaaa acaatgccgc    540
cagcggcaag gagggagggt ggaaacacat gccacgattc agtgtcgaat gtcctgtgat    600
cccacattca tatattttgt tattgtgtgc ctgcatccct cgcctgcttt taattcctgc    660
atcgatcctt ctttgctcct ggtctacgaa cccgatgtct tatggtaatt ttatgattat    720
tacaattaga ttcgggggaa actgcatctg ccgccgtctg cagatccgat tcatttggat    780
tccgtctgct caatccagat ccatgatggg atcatggcca tttgggcatt ggtacatgga    840
aagttaaaag cgccctaggc gttctaatcc aactcgtctc aagaaaaacg ggtgaatgca    900
tggaacgctg gatctggttc tggaagatcc ggctaagtac acaagaaata tgtaacctcg    960
ccattatagc tttactttcg aagcagaaaa tgcaatcgag aatatcgaat gcacgctcca   1020
ggttcctatg gctcctagct ttcggtgcag cacaacaaat atttgggttg gttcgttttt   1080
ccgccacgat tttaaaacgc taagggtggc ttttcggag tccctctcat ttgagccggg   1140
```

-continued

```
aaaaagacca gaccctccct ttccctcccc agccactttc cagctttgtt gtaacctcgt    1200
gttgtgcctg cttttaatc ccgctttgtt gtaacgcagg ccatttgctg tttttgtttt    1260
gtttctggcg tggctaaaac ggattatgtg acccaaccct ttcgatttcg agtctcattg    1320
tattacatcc ttttcccaaa aatgactaaa aaagcgtatt gcctatttct ggggtggaca    1380
gaatgaaacg gggtcagcac gtggccgcaa acttgaaata ccattatgga tccaatagga    1440
ctgtgaagag ttattagtga aacatttcga acaaactatt cctttaattg aaatttgcca    1500
attccccact taagcatcgc atttgcatat ttgtatgcta accaaactct ctgcgacgtc    1560
gatctgtctg aatctgaatc cgcatatctt tcgagggcag caatagcgcc accccacccc    1620
atttccgttg ccactagcag cgcaccaccc tttgaaagga catcaaaaac cacccctgc     1680 ccaaagttgc gttacaattc ccgaagtgca gtgcagcgta cataaacat acaatgaaat     1740 ccgataaaat tttctatgtc ctttatatcc tcataacatg cccaactata aaccgagcca    1800
aattcttctc gtgaaaaagt tgcacacaac gcgatttcac tgtaccttac attgttctgt    1860
aaactggaac agagcgtccg actggaagag gcgaaggaaa aaatcagcac agggaacagg    1920
aagttcacaa ggattggggg tgtccgaggg tggctacata tatatggcga tatatggcat    1980
acagtatgtg catacatata catacatata cacatatatg tatgtatgta ccatactatg    2040
tggcgtgtct agtggcgcga ataacgaata caggagcaat gaagcacacg aacgaagcga    2100
aacgaaacga agggaaatat tgaaaaagcc agaattgcat tacttcaaaa ctataccggc    2160
tcttggatat gggtcctggg tctcggttcc ttgcttctgg ctttcgcttc gtaggggtg     2220 tacgagcaat actgccagga gaaaccaccc tagcctttgg cgttggtggt tgatagtgca    2280
aaaataataa taacggaaac ggaaccataa acccaaaaca gcccttacaa cgcgactgat    2340
ttgtaaggat aatggtcgca tgcatcataa aacggttgac gacctcgtcg gaaagagcca    2400 acatttgca atgatttcca attgctcctg ctatctaggc ccaatgggcc gctaagtaca     2460
tatgaagcat acatagctaa atacatatga agcatacata catcgggtta actataaaac    2520
caatgtgttc tagatgagtt tgttaatttt acaaagtaag ttagggctgc tccagtggtt    2580
ttaagttgct taactggaca agagaacttg gctctctccc ccatctatct cttgtcttcg    2640
ggaaaggtaa cctccatttt gatcggttga atttgtatca aaagcatga aaaactttga     2700 atacagcata aaccactgag agagcagccg aaagccaggg gtgtatcaaa aggggttctt    2760
agaaatattc cactttgcaa cgattataga ctcgtttctt atcagacaaa actttctcca    2820
cttctacgtg gtatttacag aaacaaaact taaggtaaaa tgttaggtgg ctatatatta    2880
aagctattaa aatatattaa aggtttccgg aataaccccc tatctcggcg cgcagatacg    2940
cccatgtcgc cactctttcg ctctctacct tccactctcg ctccgaacac cattgcaacc    3000
ccgagagagc tgctcgagag gcaactatga gatatgagaa tgagaggttg ctctatgtga    3060
aaatggaaac cgaaaccgtc aatgcctcaa tttcgcattt cattatttca tttccacgcc    3120
aaccatcgtg cgccgcggtc tgaacgctcc tgccacagaa aaagaagata aaagcaagga    3180
aaattctaat cgaataccaa atatcgtgct tgtgtgctct ttccgcaatt gatttttttt    3240
aagtagtgca tgcaataac cgttgagttg actccaaccg aagtaaccat aactggaagc     3300
tgacaacagc cattggccgg aatctcatct cacaccgagc gaaatacggc gacgccagcg    3360
tttatttatt aaaaacgatt acattacaac aaacaccaaa gtcctggaca accgaagaga    3420
gtgtgggaga aaatcgaagc agagagcaag gaggagcgcc gtgagagcgc gcgcgcaagg    3480
atttgagatt gcaaagagaa cttagcaatt agttcgcttt gtttgtccag ccaaacaaca    3540
```

```
acaacaacca accagctccc caaaaccaac tacacacata ctcgctccct aaactaaaac   3600
aatagaattc aaaatggggg agaaacccgg gaccagggtc ttcaagaagt cgagccctaa   3660
ctgcaagctc accgtgtact tgggcaagcg ggacttcgta gatcacctgg acaaagtgga   3720
ccctgtagat ggcgtggtgc ttgtggaccc tgactacctg aaggaccgca aagtgtttgt   3780
gaccctcacc tgcgccttcc gctatggccg tgaagacctg gatgtgctgg cttgtccttt   3840
ccgcaaagac ctgttcatcg ccacctacca ggccttcccc ccggtgccca cccaccccg    3900
gcccccacc cgcctgcagg accggctgct gaggaagctg ggccagcatg cccaccccctt   3960
cttcttcacc atacccagaa atcttccatg ctccgtcaca ctgcagccag cccagaggaa   4020
tacaggaaag gcctgcggcg tagactttga gattcgagcc ttctgtgcta aatcactaga   4080
agagaaaagc cacaaaagga actctgtgcg gctggtgatc cgaaaggtgc agttcgcccc   4140
ggagaaaccc ggccccagc cttcagccga aaccacacgc cacttcctca tgtctgaccg    4200
gtccctgcac ctcgaggctt ccctggacaa ggagctgtac taccatgggg agcccctcaa   4260
tgtaaatgtc cacgtcacca acaactccac caagaccgtc aagaagatca agtctctgt    4320
gagacagtac gccgacatct gcctcttcag caccgcccag tacaagtgtc ctgtggctca   4380
actcgaacaa gatgaccagg tatctcccag ctccacattc tgtaaggtgt acaccataac   4440
cccactgctc agtgacaacc gggagaagcg gggtctcgcc ctggatggga aactcaagca   4500
cgaggacacc aacctggctt ccagcaccat cgtgaaggag ggtgccaaca aggaggtgct   4560
gggaatcctg gtgtcctaca gggtcaaggt gaagctggtg gtgtctcgag gcggggatgt   4620
ctctgtggag ctgcctttg ttcttatgca ccccaagccc cacgaccaca tccccctccc    4680
cagaccccag tcagccgctc cggagacaga tgtccctgtg acaccaacc tcattgaatt    4740
tgataccaac tatgccacag atgatgacat tgtgtttgag gactttgccc ggcttcggct   4800
gaaggggatg aaggatgacg actatgatga tcaactctgc ggatctagct tgtttaaggg   4860
accacgtgat tacaacccga tatcgagcac catttgtcat ttgacgaatg aatctgatgg   4920
gcacacaaca tcgttgtatg gtattggatt tggtcccttc atcattacaa acaagcactt   4980
gtttagaaga aataatggaa cactgttggt ccaatcacta catggtgtat tcaaggtcaa   5040
gaacaccacg actttgcaac aacacctcat tgatgggagg gacatgataa ttattcgcat   5100
gcctaaggat ttcccaccat ttcctcaaaa gctgaaattt agagagccac aaagggaaga   5160
gcgcatatgt cttgtgacaa ccaacttcca aactaagagc atgtctagca tggtgtcaga   5220
cactagttgc acattccctt catctgatgg catattctgg aagcattgga ttcaaaccaa   5280
ggatgggcag tgtggcagtc cattagtatc aactagagat gggttcattg ttggtataca   5340
ctcagcatcg aatttcacca acacaaacaa ttatttcaca agcgtgccga aaacttcat    5400
ggaattgttg acaagtcagg aggcgcagca gtgggttagt ggttggcgat taaatgctga   5460
ctcagtattg tgggggggcc ataaagtttt catgagcaaa cctgaagagc ttttcagcc    5520
agttaaggaa gcgactcaac tcatgaatga attggtgtac tcgtgaagat ctggatcttt   5580
gtgaaggaac cttacttctg tggtgtgaca taattggaca aactacctac agagatttaa   5640
agctctaagg taaatataaa atttttaagt gtataatgtg ttaaactact gattctaatt   5700
gtttgtgtat tttagattcc aacctatgga actgatgaat gggagcagtg gtggaatgcc   5760
tttaatgagg aaaacctgtt ttgctcagaa gaaatgccat ctagtgatga tgaggctact   5820
gctgactctc aacattctac tcctccaaaa aagaagagaa aggtagaaga ccccaaggac   5880
```

| | |
|---|---|
| tttccttcag aattgctaag ttttttgagt catgctgtgt ttagtaatag aactcttgct | 5940 |
| tgctttgcta tttacaccac aaaggaaaaa gctgcactgc tatacaagaa aattatggaa | 6000 |
| aaatatttga tgtatagtgc cttgactaga gatcataatc agccatacca catttgtaga | 6060 |
| ggttttactt gctttaaaaa acctcccaca cctcccctg aacctgaaac ataaaatgaa | 6120 |
| tgcaattgtt gttgttaact tgtttattgc agcttataat ggttacaaat aaagcaatag | 6180 |
| catcacaaat ttcacaaata aagcattttt tcactgcat tctagttgtg gtttgtccaa | 6240 |
| actcatcaat gtatcttatc atgtct | 6266 |

<210> SEQ ID NO 4
<211> LENGTH: 2253
<212> TYPE: DNA
<213> ORGANISM: Artificial Sequence
<220> FEATURE:
<223> OTHER INFORMATION: Synthetic Construct

<400> SEQUENCE: 4

| | |
|---|---|
| gggtaatcgc ttatcctcgg ataaacaatt atcctcacgg gtaatcgctt atccgctcgg | 60 |
| gtaatcgctt atcctcgggt aatcgcttat ccttaagctt gatatcgaat tcctgcagcc | 120 |
| cgagcggaga ctctagcgag cgccggagta taaatagagg cgcttcgtct acggagcgac | 180 |
| aattcaattc aaacaagcaa agtgaacacg tcgctaagcg aaagctaagc aaataaacaa | 240 |
| gcgcagctga acaagctaaa caatctgcag taaagtgcaa gttaaagtga atcaattaaa | 300 |
| agtaaccagc aaccaagtaa atcaactgca actactgaaa tctgccaaga agtaattatt | 360 |
| gaatacaaga agagaactct gaatagggaa ttgggaattc gttaacagat cggggggatca | 420 |
| attcgttaac agatccatgg gttgctgttt ctccaagacc atggtgagca agggagagga | 480 |
| ggtcatcaaa gagttcatgc gcttcaaggt gcgcatggag ggctccatga acggccacga | 540 |
| gttcgagatc gagggcgagg gcgagggccg cccctacgag ggcacccaga ccgccaagct | 600 |
| gaaggtgacc aagggcggcc ccctgccctt cgcctgggac atcctgtccc ccagttcat | 660 |
| gtacggctcc aaggcgtacg tgaagcaccc cgccgacatc cccgattaca agaagctgtc | 720 |
| cttccccgag ggcttcaagt gggagcgcgt gatgaacttc gaggacggcg gtctggtgac | 780 |
| cgtgacccag gactcctccc tgcaggacgg cacgctgatc tacaaggtga agatgcgcgg | 840 |
| caccaacttc ccccccgacg gccccgtaat gcagaagaag accatgggct gggaggcctc | 900 |
| caccgagcgc ctgtacccc gcgacggcgt gctgaagggc gagatccacc aggccctgaa | 960 |
| gctgaaggac ggcggccact acctggtgga gttcaagacc atctacatgg ccaagaagcc | 1020 |
| cgtgcaactg cccggctact actacgtgga caccaagctg gacatcacct cccacaacga | 1080 |
| ggactacacc atcgtggaac agtacgagcg ctccgagggc cgccaccacc tgttcctggg | 1140 |
| gcatggcacc ggcagcaccg gcagcggcag ctccggcacc gcctcctccg aggacaacaa | 1200 |
| catggccgtc atcaaagagt tcatgcgctt caaggtgcgc atggagggct ccatgaacgg | 1260 |
| ccacgagttc gagatcgagg gcgagggcga gggccgcccc tacgagggca cccagaccgc | 1320 |
| caagctgaag gtgaccaagg gcggcccct gcccttcgcc tgggacatcc tgtccccca | 1380 |
| gttcatgtac ggctccaagg cgtacgtgaa gcaccccgcc gacatcccg attacaagaa | 1440 |
| gctgtccttc cccgagggct tcaagtggga gcgcgtgatg aacttcgagg acggcggtct | 1500 |
| ggtgaccgtg acccaggact cctccctgca ggacggcacg ctgatctaca aggtgaagat | 1560 |
| gcgcggcaca aacttccccc ccgacggccc cgtaatgcag aagaagacca tgggctggga | 1620 |
| ggcctccacc gagcgcctgt accccgcga cggcgtgctg aagggcgaga tccaccaggc | 1680 |

```
cctgaagctg aaggacggcg gccgctacct ggtggagttc aagaccatct acatggccaa      1740
gaagcccgtg caactgcccg gctactacta cgtggacacc aagctggaca tcacctccca      1800
caacgaggac tacaccatcg tggaacagta cgagcgctcc gagggccgcc accacctgtt      1860
cctgtacggc atggacgagc tgtacaagta cccatacgat gttcctgact atgcgggcta      1920
tccctatgac gtcccggact atgcaggatc ctatccatat gacgttccag attacgctta      1980
agaattcgat atcaagtatc gataccgtcg actaaagcca aatagaaaat tattcagttc      2040
ctggcttaag ttttaaaag tgatattatt tatttggttg taaccaacca aaagaatgta       2100
aataactaat acataattat gttagtttta agttagcaac aaattgattt tagctatatt      2160
agctacttgg ttaataaata gaatatattt atttaaagat aattgcgttt ttattgtcag      2220
ggagtgagtt tgcttaaaaa ctcgtttaga tcc                                   2253

<210> SEQ ID NO 5
<211> LENGTH: 2298
<212> TYPE: DNA
<213> ORGANISM: Artificial Sequence
<220> FEATURE:
<223> OTHER INFORMATION: Synthetic Construct

<400> SEQUENCE: 5
gcatgcctgc aggtcggagt actgtcctcc gagcggagta ctgtcctccg agcggagtac        60
tgtcctccga gcggagtact gtcctccgag cggagtactg tcctccgagc ggagactcta      120
gccctagggc atgcctgcag gtcggagtac tgtcctccga gcggagtact gtcctccgag      180
cggagtactg tcctccgagc ggagtactgt cctccgagcg gagtactgtc ctccgagcgg      240
agactctagc gctagcgacg tcgagcgccg gagtataaat agaggcgctt cgtctacgga      300
gcgacaattc aattcaaaca gcaaagtgaa acacgtcgct aagcgaaagc taagcaaata      360
aacaagcgca gctgaacaag ctaaacaatc tgcagtaaag tgcaagttaa agtgaatcaa      420
ttaaaagtaa ccagcaacca gtaaatcaa ctgcaactac tgaaatctgc caagaagtaa       480
ttattgaata caagaagaga actctgaata gatctaaaag gtaggttcaa ccactgatgc      540
ctaggcacac cgaaacgact aaccctaatt cttatccttt acttcaggcg gccgcggctc      600
gagaatcaaa atgggcaaca atgctgcag caagcgacag gatcaggaac tggcactggc       660
ctatcccact gggggctaca agaaatccga ctacaccttt ggccagacgc acatcaacag      720
cagcggcggc ggcaacatgg gcggcgttct tggccagaag cataacaacg gtggctcgct      780
ggactcgcgc tacacgcccg atcccaatca tcggggtccg ttgaaaatcg gcggaaaggg      840
cggcgttgac atcatcagac cacgcggatc catgtccaaa ggtgaagaac tgtttaccgg      900
agtagtcccg atattggttg aactcgacgc gatgtcaac ggtcataaat tcagtgtgtc       960
cggcgagggt gagggcgacg ccacatacgg taagctgacg ttgaagttca tatgcaccac     1020
gggcaagctg cccgtgccat ggccgacgtt ggtcacgacg ctgacgtatg gtgtccagtg     1080
tttcagccgt taccccgatc atatgaagca gcatgacttt ttcaagtcgg cgatgccgga     1140
gggatacgtt caagagagga ccattttctt caaggatgac ggcaactata agacgcgagc     1200
ggaggtgaaa tttgaaggcg acacactcgt taaccgtatt gagttgaagg gcattgattt     1260
taaggaggat ggcaacattc tgggccataa gttggaatac aactacaact cgcataatgt     1320
gtatataatg gcagataagc agaaaaacgg aataaaggtt aacttcaaga ttcgccacaa     1380
catagaggac ggttccgtgc aacttgcaga tcattaccaa cagaacacac ccattggaga     1440
```

-continued

```
tggcccagtt ctcttgccag acaatcacta cctttccaca cagtccgcgt tgagcaagga   1500
ccccaatgaa aagcgggacc acatggtgtt gctggagttt gtgaccgcag ctggtattac   1560
acacggcatg gatgagctct acaagtaatc tagaggatct ttgtgaagga accttacttc   1620
tgtggtgtga cataattgga caaactacct acagagattt aaagctctaa ggtaaatata   1680 aaattttaa gtgtataatg tgttaaacta ctgattctaa ttgtttgtgt attttagatt    1740
ccaacctatg gaactgatga atgggagcag tggtggaatg cctttaatga ggaaaacctg   1800
ttttgctcag aagaaatgcc atctagtgat gatgaggcta ctgctgactc tcaacattct   1860
actcctccaa aaaagaagag aaaggtagaa gaccccaagg actttccttc agaattgcta   1920
agttttttga gtcatgctgt gtttagtaat agaactcttg cttgctttgc tatttacacc   1980
acaaaggaaa aagctgcact gctatacaag aaaattatgg aaaaatattt gatgtatagt   2040
gccttgacta gagatcataa tcagccatac cacatttgta gaggttttac ttgctttaaa   2100
aaacctccca cacctccccc tgaacctgaa acataaaatg aatgcaattg ttgttgttaa   2160
cttgtttatt gcagcttata atggttacaa ataaagcaat agcatcacaa atttcacaaa   2220
taaagcattt ttttcactgc attctagttg tggtttgtcc aaactcatca atgtatctta   2280
tcatgtctgg atcgatct                                                 2298
```

<210> SEQ ID NO 6
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 6

Gly Gly Gly
1

<210> SEQ ID NO 7
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 7

Gly Gly Gly Gly Ser
1               5

<210> SEQ ID NO 8
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 8

Gly Gly Ser Gly
1

<210> SEQ ID NO 9
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 9

```
Ser Gly Gly Gly
1

<210> SEQ ID NO 10
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 10

Gly Ser Gly Ser
1

<210> SEQ ID NO 11
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 11

Gly Ser Gly Ser Gly Ser
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 12

Gly Ser Gly Ser Gly Ser Gly Ser
1               5

<210> SEQ ID NO 13
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 13

Gly Ser Gly Ser Gly Ser Gly Ser Gly Ser
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 14

Gly Ser Gly Ser Gly Ser Gly Ser Gly Ser Gly Ser
1               5                   10

<210> SEQ ID NO 15
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 15

Gly Gly Ser Gly Gly Ser
```

```
<210> SEQ ID NO 16
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 16

Gly Gly Ser Gly Gly Ser Gly Gly Ser
1               5

<210> SEQ ID NO 17
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 17

Gly Gly Ser Gly Gly Ser Gly Gly Ser Gly Gly Ser
1               5                   10

<210> SEQ ID NO 18
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 18

Gly Gly Ser Gly
1

<210> SEQ ID NO 19
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 19

Gly Gly Ser Gly Gly Gly Ser Gly
1               5

<210> SEQ ID NO 20
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 20

Gly Gly Ser Gly Gly Gly Ser Gly Gly Gly Ser Gly
1               5                   10

<210> SEQ ID NO 21
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 21

Gly Gly Gly Gly Ser
1               5
```

<210> SEQ ID NO 22
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 22

Gly Gly Gly Gly Ser Gly Gly Gly Gly Ser Gly Gly Gly Gly Ser
1               5                   10                  15

<210> SEQ ID NO 23
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 23

Gly Asn Gly Asn Gly Asn Gly Asn Gly Asn Gly Asn Gly Asn Gly Asn
1               5                   10                  15

Gly Asn

<210> SEQ ID NO 24
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 24

Gly Asn Gly Asn Gly Asn Gly Asn Gly Thr Gly
1               5                   10

<210> SEQ ID NO 25
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 25

Gly Gly Gly Gly Ala Gly Gly Gly Gly
1               5

<210> SEQ ID NO 26
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 26

Gly Glu Asn Leu Tyr Phe Gln Ser Gly Gly
1               5                   10

<210> SEQ ID NO 27
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 27

Ser Ala Cys Tyr Cys Glu Leu Ser

```
<210> SEQ ID NO 28
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 28

Arg Ser Ile Ala Thr
1               5

<210> SEQ ID NO 29
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 29

Arg Pro Ala Cys Lys Ile Pro Asn Asp Leu Lys Gln Lys Val Met Asn
1               5                   10                  15

His

<210> SEQ ID NO 30
<211> LENGTH: 36
<212> TYPE: PRT
<213> ORGANISM: Artificial Sequence
<220> FEATURE:
<223> OTHER INFORMATION: Synthetic Peptide

<400> SEQUENCE: 30

Gly Gly Ser Ala Gly Gly Ser Gly Ser Gly Ser Ser Gly Gly Ser Ser
1               5                   10                  15

Gly Ala Ser Gly Thr Gly Thr Ala Gly Gly Thr Gly Ser Gly Ser Gly
                20                  25                  30

Thr Gly Ser Gly
        35

<210> SEQ ID NO 31
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 31

Ala Ala Ala Asn Ser Ser Ile Asp Leu Ile Ser Val Pro Val Asp Ser
1               5                   10                  15

Arg

<210> SEQ ID NO 32
<211> LENGTH: 36
<212> TYPE: PRT
<213> ORGANISM: Artificial Sequence
<220> FEATURE:
<223> OTHER INFORMATION: Synthetic Peptide

<400> SEQUENCE: 32

Gly Gly Ser Gly Gly Gly Ser Glu Gly Gly Ser Glu Gly Gly Gly
1               5                   10                  15

Ser Glu Gly Gly Gly Ser Glu Gly Gly Gly Ser Glu Gly Gly Gly Ser
                20                  25                  30
```

```
Gly Gly Gly Ser
        35

<210> SEQ ID NO 33
<211> LENGTH: 7
<212> TYPE: PRT
<213> ORGANISM: Artificial Sequence
<220> FEATURE:
<223> OTHER INFORMATION: Synthetic Construct

<400> SEQUENCE: 33

Glu Asn Leu Tyr Phe Gln Ser
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic Construct

<400> SEQUENCE: 34

Glu Asn Leu Tyr Phe Gln Tyr
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic Construct

<400> SEQUENCE: 35

Glu Asn Leu Tyr Phe Gln Leu
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic Construct

<400> SEQUENCE: 36

Asp Glu Met Glu Glu Cys Ser Gln
1               5
```

_METHODS FOR LABELING AND MANIPULATING A CELLULAR CIRCUIT_

CROSS REFERENCE TO RELATED APPLICATIONS

This application is a national phase filing under 35 U.S.C. § 371 of International Application No. PCT/US2016/022478 filed Mar. 15, 2016, which claims priority from U.S. Provisional Application No. 62/134,334, filed Mar. 17, 2015, the entire contents of which are incorporated herein by reference.

STATEMENT AS TO FEDERALLY FUNDED RESEARCH

This invention was made with government support under R21DC014333, R01MH086920, and R01MH105368, awarded by the National Institutes of Health. The government has certain rights in the invention.

REFERENCE TO A SEQUENCE LISTING

This application contains a Sequence Listing in computer readable form. The computer readable form is incorporated herein by reference.

BACKGROUND OF THE INVENTION

The abilities to identify, control, and regulate how cells communicate and transmit signals in a cellular circuit will enable researchers to better understand how cellular components work together to perform biochemical tasks, how malfunctions in these processes drive human diseases, and how to develop effective treatments.

SUMMARY OF THE INVENTION

The present invention features methods and kits useful for labeling and manipulating a cellular circuit. A cellular circuit refers to a group of interconnected cells that are arranged in a regulated network to perform a specific function. The methods and kits of the invention may be used in understanding cell-cell communication and developing effective treatments targeting human diseases, such as cancer and neurological diseases, e.g., epilepsy.

In a first aspect, the invention features a method of labeling a cellular circuit containing two or more cells, wherein the method includes: (a) transfecting a first-order cell with a first nucleic acid molecule encoding a ligand fusion polypeptide, wherein the ligand fusion polypeptide includes a membrane-targeting domain and a tethered ligand joined by way of a linker, and (b) transfecting a second-order cell with (i) a second nucleic acid molecule encoding a receptor fusion polypeptide, wherein the receptor fusion polypeptide includes a receptor, a cleavage sequence, and an effector by way of linkers, (ii) a third nucleic acid molecule encoding a protease fusion polypeptide, wherein the protease fusion polypeptide includes a receptor interactor and a protease by way of a linker, and (iii) a fourth nucleic acid molecule encoding a reporter/modifier gene under the control of an effector-responsive element, wherein the tethered ligand interacts with the receptor which induces the receptor interactor to interact with the receptor, wherein the protease cleaves the cleavage sequence to release the effector, and wherein the released effector binds to the effector-responsive element to induce the expression of the reporter/modifier gene in the second-order cell.

In a second aspect, the invention features a method of labeling a cellular circuit in a cell, wherein the method includes: (a) transfecting the cell with (i) a first nucleic acid molecule encoding a ligand fusion polypeptide, wherein the ligand fusion polypeptide includes a membrane-targeting domain and a tethered ligand joined by way of a linker, (ii) a second nucleic acid molecule encoding a receptor fusion polypeptide, wherein the receptor fusion polypeptide includes a receptor, a cleavage sequence, and an effector by way of linkers, (iii) a third nucleic acid molecule encoding a protease fusion polypeptide, wherein the protease fusion polypeptide includes a receptor interactor and a protease by way of a linker, and (iv) a fourth nucleic acid molecule encoding a reporter/modifier gene under the control of an effector-responsive element, wherein the tethered ligand interacts with the receptor to induce the receptor interactor to interact with the receptor, wherein the protease cleaves the cleavage sequence to release the effector, and wherein the released effector binds to the effector-responsive element to induce the expression of the reporter/modifier gene in the cell.

In some embodiments of either aspect, the membrane-targeting domain is a membrane bound protein or a fragment thereof. In certain embodiments, the membrane bound protein is a Neurexin (NRX1).

In some embodiments of either aspect, the tethered ligand is a ligand to a G protein-couple receptor (GPCR). In some embodiments, the tethered ligand is a peptide or non-peptide ligand. In some embodiments, the ligand is a designed synthetic ligand, which signals a GPCR or GPCR-like protein. In certain embodiments, the tethered ligand is selected from a group consisting of a human glucagon peptide, a glucose-dependent insulinotropic polypeptide (GIP), a glucagon-like peptide-1 (GLP1), a motilin peptide (MLN), a vasopressin, an oxytocin, a Bursicon, a ligand to an odorant receptor, a ligand to a visual receptor, a ligand to a β2-adrenergic receptor (ADRB2), a ligand to an arginine vasopressin receptor 2 (AVPR2), a ligand to an oxytocin receptor, a ligand to a serotonin receptor 1a (HTRIA), a ligand to a m2 muscarinic acetylcholine receptor (CHRM2), a ligand to a chemokine (C-C motif) receptor 5 (CCR5), a ligand to a dopamine D2 receptor (DRD2), a ligand to a kappa opioid receptor (OPRK), a ligand to an α1a-adregenic receptor (ADRAIA), and an analog thereof. In certain embodiments, the tethered ligand is a human glucagon peptide. In certain embodiments, the tethered ligand is an analog of human glucagon peptide.

In some embodiments of either aspect, the receptor is a transmembrane receptor (e.g., a human transmembrane receptor). In some embodiments, the transmembrane receptor is a GPCR (e.g., one selected from a group consisting of a glucagon receptor (GCGR), a glucose-dependent insulinotropic polypeptide receptor (GIPR), a glucagon-like peptide-1 receptor (GLPR), a motilin peptide receptor (MLNR), a receptor for Bursicon, an odorant receptor, a visual receptor, a β2-adrenergic receptor (ADRB2), an arginine vasopressin receptor 2 (AVPR2), an oxytocin receptor, a serotonin receptor 1a (HTRIA), a m2 muscarinic acetylcholine receptor (CHRM2), a chemokine (C-C motif) receptor 5 (CCR5), a dopamine D2 receptor (DRD2), a kappa opioid receptor (OPRK), and an ADRAIA. In certain other embodiments, the receptor is the receptor of a designed synthetic ligand-receptor pair in which a receptor protein mediates a cellular signal in response to a ligand. In certain embodiments, the receptor is a GCGR, a GIPR, a GLPR, or a MLNR. In particular embodiments, the receptor is a GCGR.

In some embodiments, the cleavage sequence is ENLYFQS (SEQ ID NO: 33), ENLYFQY (SEQ ID NO: 34), ENLYFQL (SEQ ID NO: 35), or DEMEECSQ (SEQ ID NO: 36).

In some embodiments, the effector is a transcription factor. In certain embodiments, the transcription factor is tTA, tTA2, Gal4, LexA, or QF.

In some embodiments, the receptor interactor is an inhibitory protein. In certain embodiments, the inhibitory protein is an arrestin.

In some embodiments, the protease is tobacco etch virus nuclear inclusion A (TEV) protease. In some embodiments, the protease is the nonstructural protein 3 protease domain of the hepatitis C virus (NS3 HCV).

In some embodiments, the nucleotide sequence encoding the receptor is modified to increase interaction of the receptor with the receptor interactor. In certain embodiments, the modification includes replacing all or part of the nucleotide sequence of a C-terminal region of the receptor with a nucleotide sequence which encodes an amino acid sequence which has higher affinity for the receptor interactor than the original sequence. In certain embodiments, the nucleotide sequence of the C-terminal region of the receptor is replaced by a nucleotide sequence encoding all or a part of the C-terminal region of an AVPR2, an angiotensin receptor-like 1 (AGTRL1), a gastrin-releasing peptide receptor (GRPR), an F2PL1, a chemokine (C-X-C motif) receptor (CXCR2/IL-8B), or a chemokine (C-C motif) receptor 4 (CCR4).

In some embodiments, the nucleotide sequence encoding the receptor is modified to mutate downstream signaling. For example, a GPCR (e.g., a GCGR, a GIPR, a GLPR, a MLNR, a receptor for Bursicon, an odorant receptor, a visual receptor, an ADRB2, an AVPR2, an oxytocin receptor, a HTRIA, a CHRM2, a CCR5, a DRD2, a OPRK, and an ADRAIA) may be modified to disrupt downstream signaling. In some embodiments, the nucleotide sequence encoding the GPCR or a part thereof is modified to increase or decrease interaction of the GPCR with the receptor interactor. In some embodiments, the nucleotide sequence encoding an intracellular loop of the GPCR is modified. In certain embodiments, the modification includes replacing part of the nucleotide sequence of the second intracellular loop (between the third and fourth transmembrane regions) of a GPCR with a nucleotide sequence that encodes an amino acid sequence that mutates downstream signaling of the receptor. For example, modifying an intracellular loop (e.g., the second intracellular loop between the third and fourth transmembrane regions) of a GPCR may change the interaction between an activated GPCR and its receptor interactor (e.g., β-arrestin). In some embodiments, modifying the intracellular of the GPCR may increase the affinity between an activated GPCR and its receptor interactor. In other embodiments, modifying the loop may decrease the affinity between an activated GPCR and its receptor interactor.

In some embodiments, the reporter/modifier gene is an exogenous gene. In certain embodiments, the exogenous gene encodes mtdTomato.

In some embodiments, the ligand fusion polypeptide further includes an extracellular spacer domain between the membrane-targeting domain and the tethered ligand. In certain embodiments, the extracellular spacer domain is the extracellular domain of a human intercellular adhesion molecule 1 (ICAM1) or a splice variant thereof.

In a third aspect, the invention features a kit useful for labeling a cellular circuit containing two or more cells, the kit includes: (a) a first nucleic acid molecule encoding a ligand fusion polypeptide, wherein the ligand fusion polypeptide includes a membrane-targeting domain and a tethered ligand by way of a linker, (b) a second nucleic acid molecule encoding a receptor fusion polypeptide, wherein the receptor fusion polypeptide includes a receptor, a cleavage sequence, and an effector by way of linkers, (c) a third nucleic acid molecule encoding a protease fusion polypeptide, wherein the protease fusion polypeptide includes a receptor interactor and a protease by way of a linker, (d) a fourth nucleic acid molecule encoding a reporter/modifier gene under the control of an effector-responsive element, and (e) a container for holding each of (a)-(d) separately from each other.

In some embodiments of the third aspect of the invention, the membrane-targeting domain is a membrane bound protein or a fragment thereof. In certain embodiments, membrane bound protein is a NRX1.

In some embodiments, the tethered ligand is a ligand to a GPCR. In some embodiments, tethered ligand is a peptide or non-peptide ligand. In some embodiments, the ligand is a designed synthetic ligand, which signals a GPCR or GPCR-like protein. In some embodiments, tethered ligand is selected from a group consisting of a glucagon peptide, a GIP, a GLP1, a MLN, a vasopressin, an oxytocin, a Bursicon, a ligand to an odorant receptor, a ligand to a visual receptor, a ligand to a β2-adrenergic receptor (ADRB2), a ligand to an arginine vasopressin receptor 2 (AVPR2), a ligand to an oxytocin receptor, a ligand to a serotonin receptor 1a (HTRIA), a ligand to a m2 muscarinic acetylcholine receptor (CHRM2), a ligand to a chemokine (C-C motif) receptor 5 (CCR5), a ligand to a dopamine D2 receptor (DRD2), a ligand to a kappa opioid receptor (OPRK), a ligand to an α1a-adregenic receptor (ADRAIA), and an analog thereof.

In some embodiments, the tethered ligand is a human glucagon peptide or an analog thereof.

In some embodiments of the third aspect of the invention, the receptor is a transmembrane receptor. In certain embodiments, the transmembrane receptor is selected from a group consisting of a GPCR, a human glucagon receptor (GCGR), a glucose-dependent insulinotropic polypeptide receptor (GIPR), a glucagon-like peptide-1 receptor (GLPR), a motilin peptide receptor (MLNR), a receptor for Bursicon, an odorant receptor, a visual receptor, a β2-adrenergic receptor (ADRB2), an arginine vasopressin receptor 2 (AVPR2), an oxytocin receptor, a serotonin receptor 1a (HTRIA), a m2 muscarinic acetylcholine receptor (CHRM2), a chemokine (C-C motif) receptor 5 (CCR5), a dopamine D2 receptor (DRD2), a kappa opioid receptor (OPRK), and an ADRAIA. In certain other embodiments, the receptor is the receptor of a designed synthetic ligand-receptor pair in which a receptor protein mediates a cellular signal in response to a ligand. In certain embodiments, the receptor is a GPCR, GCGR, a GIPR, a MLNR, or a GLPR. In particular embodiments, the receptor is a GCGR.

In some embodiments, the cleavage sequence is ENLYFQS (SEQ ID NO: 33), ENLYFQY (SEQ ID NO: 34), ENLYFQL (SEQ ID NO: 35), or DEMEECSQ (SEQ ID NO: 36).

In some embodiments, the effector is a transcription factor. In certain embodiments, the transcription factor is tTA, tTA2, Gal4, LexA, or QF.

In some embodiments of the third aspect of the invention, the receptor interactor is an inhibitory protein. In certain embodiments, the inhibitory protein is an arrestin.

In some embodiments of the third aspect of the invention, the protease is tobacco etch virus nuclear inclusion A (TEV) protease. In some embodiments, the protease is the non-structural protein 3 protease domain of the hepatitis C virus (NS3 HCV).

In some embodiments of the third aspect of the invention, the nucleotide sequence encoding the receptor is modified to increase interaction of the receptor with the receptor interactor. In certain embodiments, the modification includes replacing all or part of the nucleotide sequence of a C-terminal region of the receptor with a nucleotide sequence which encodes an amino acid sequence which has higher affinity for the receptor interactor than the original sequence. In certain embodiments, the nucleotide sequence of the C-terminal region of the receptor is replaced by a nucleotide sequence encoding all or a part of the C-terminal region of an AVPR2, an angiotensin receptor-like 1 (AGTRL1), a gastrin-releasing peptide receptor (GRPR), an F2PL1, a chemokine (C-X-C motif) receptor (CXCR2/IL-8B), or a chemokine (C-C motif) receptor 4 (CCR4).

In some embodiments, the nucleotide sequence encoding the receptor is modified to mutate downstream signaling. For example, a GPCR (e.g., a GCGR, a GIPR, a GLPR, a MLNR, a receptor for Bursicon, an odorant receptor, a visual receptor, an ADRB2, an AVPR2, an oxytocin receptor, a HTR1A, a CHRM2, a CCR5, a DRD2, a OPRK, and an ADRA1A) may be modified to disrupt downstream signaling. In some embodiments, the nucleotide sequence encoding the GPCR or a part thereof is modified to increase or decrease interaction of the GPCR with the receptor interactor. In some embodiments, the nucleotide sequence encoding an intracellular loop of the GPCR is modified. In certain embodiments, the modification includes replacing part of the nucleotide sequence of the second intracellular loop (between the third and fourth transmembrane regions) of a GPCR with a nucleotide sequence that encodes an amino acid sequence that mutates downstream signaling of the receptor. For example, modifying an intracellular loop (e.g., the second intracellular loop between the third and fourth transmembrane regions) of a GPCR may change the interaction between an activated GPCR and its receptor interactor (e.g., β-arrestin). In some embodiments, modifying the intracellular of the GPCR may increase the affinity between an activated GPCR and its receptor interactor. In other embodiments, modifying the loop may decrease the affinity between an activated GPCR and its receptor interactor.

In some embodiments, the reporter/modifier gene is an exogenous gene. In certain embodiments, the exogenous gene encodes mtdTomato.

In a fourth aspect, the invention features a method of assaying the activation of a receptor by a ligand. This method includes the steps of: (a) transfecting a first-order cell with a nucleic acid molecule encoding a ligand fusion polypeptide, wherein the ligand fusion polypeptide includes a membrane-targeting domain and the ligand joined by way of a linker, and (b) transfecting a second-order cell with (i) a second nucleic acid molecule encoding a receptor fusion polypeptide, wherein the receptor fusion polypeptide includes the receptor, a cleavage sequence, and an effector by way of linkers, (ii) a third nucleic acid molecule encoding a protease fusion polypeptide, wherein the protease fusion polypeptide includes a receptor interactor and a protease by way of a linker, and (iii) a fourth nucleic acid molecule encoding a reporter/modifier gene under the control of an effector-responsive element, and (c) measuring the expression of the reporter/modifier gene in the second-order cell.

In a fifth aspect, the invention features another method of assaying the activation of a receptor by a ligand. This method includes the steps of: (a) transfecting a cell with (i) a nucleic acid molecule encoding a ligand fusion polypeptide, wherein the ligand fusion polypeptide includes a membrane-targeting domain and the ligand joined by way of a linker, (ii) a second nucleic acid molecule encoding a receptor fusion polypeptide, wherein the receptor fusion polypeptide includes the receptor, a cleavage sequence, and an effector by way of linkers, (iii) a third nucleic acid molecule encoding a protease fusion polypeptide, wherein the protease fusion polypeptide includes a receptor interactor and a protease by way of a linker, and (iv) a fourth nucleic acid molecule encoding a reporter/modifier gene under the control of an effector-responsive element, and (b) measuring the expression of the reporter/modifier gene in the cell.

In the fourth and fifth aspects of the invention, if the potential ligand binds and interacts with (e.g., activates) the receptor in the receptor fusion polypeptide, the receptor interactor is induced to interact with the activated receptor, the protease cleaves the cleavage sequence to release the effector, and the released effector binds to the effector-responsive element to induce the expression of the reporter/modifier gene.

In the fourth and fifth aspects of the invention, the expression of the reporter/modifier gene can be measured, e.g., by fluorescence.

In the fourth and fifth aspects of the invention, the reporter/modifier gene is an exogenous gene. In some embodiments, the exogenous gene encodes a fluorescent protein or luciferase protein. In some embodiments, the protein is mtdTomato. In some embodiments, the reporter/modifier gene is a growth-promoting gene that increases the growth or reproduction of the cell. In some embodiments, the growth-promoting gene is involved in the synthesis of a nucleotide, an amino acid, or a molecule within the cell. In some embodiments, the reporter/modifier gene confers resistance to a molecule (e.g., an antibiotic) that inhibits growth or reproduction of the cell.

Definitions

As used herein, the term "cellular circuit" refers to a cell or a group of interconnected cells that are arranged in a regulated network to perform a specific function. Generally, the cells in a cellular circuit communicate with each other using biological signals transmitted through, e.g., receptors (e.g., a transmembrane receptor), ligands, chemical and electrical gradients. For example, the network of interconnected neurons in the nervous system, e.g., the brain, forms a neuronal circuit along which electrical and chemical signals travel such that the neurons are able to perform a task together. As a single cell can signal to itself, a single cell can constitute a cellular circuit.

As used herein, the term "labeling" or "label" refers to the act of making the cells in a cellular circuit detectable and/or traceable, making the labeled cells distinguishable from other surrounding cells, e.g., other cells that do not belong in the specific cellular circuit, and/or controlling the signaling and/or cell fate of specific cells in the cellular circuit. Labeling a cellular circuit makes it possible to trace from a first-order cell in the circuit to a second-order cell in the same circuit. In some embodiments, labeling a cellular circuit can activate or inhibit the signaling from one cell to the next cell, thus, affecting certain protein expressions, cell fates, and genotype and/or phenotype of the cell, tissue, or organ as a whole.

As used herein, the term "first-order cell" refers to a cell or a group of cells where the labeling or manipulation of a cellular circuit first starts. The first-order cell expresses the ligand fusion polypeptide. For example, in a neuronal circuit, the first-order cell may be a pre-synaptic neuron.

As used herein, the term "second-order cell" refers to a cell or a group of cells where the signal sent by the first-order cell is received. The "signal" here may be the interaction between the tethered ligand expressed in the first-order cell and its target receptor expressed in the second-order cell. For example, in a neuronal circuit, the second-order cell may be a post-synaptic neuron.

As used herein, the term "ligand" refers to a molecule that has the affinity to bind to a second molecule, such as a receptor. In some embodiments, a ligand is tethered (a tethered ligand) to the cell membrane by, e.g., a membrane-targeting domain, such that the ligand faces the outside of the cell. In some embodiments, a ligand and its target receptor are in different cells. In some embodiments, a ligand is one of the protein partners in a two-protein binding pair.

As used herein, the term "membrane-targeting domain" refers to a protein, peptide, or fragment thereof that is attached to or associated with the cell membrane. An example of a membrane-targeting domain is a membrane bound protein. In the ligand fusion polypeptide, the membrane-targeting domain serves to target the tethered ligand to the cell membrane.

As used herein, the term "ligand fusion polypeptide" refers to a fusion of a membrane-targeting domain and a tethered ligand joined in tandem series by way of a linker. In the present invention, the ligand fusion polypeptide is expressed in the first-order cell in a cellular circuit. The tethered ligand interacts with the receptor in the second-order cell in the cellular circuit. In some embodiments, the ligand fusion polypeptide further includes an extracellular spacer domain.

As used herein, the term "extracellular spacer domain" refers to a protein, peptide, or fragment that is inserted between the membrane-targeting domain and the tethered ligand in the ligand fusion polypeptide. The extracellular spacer domain serves to extend or place the ligand in the first-order cell at an optimal position to interact with the receptor in the second-order cell. The protein, peptide, or fragment thereof that is chosen to serve as the extracellular spacer domain depends on the distance and/or flexibility that is needed to facilitate the interaction between the ligand and the receptor.

As used herein, the term "receptor" refers to a molecule that is specifically bound by one or more particular ligands. The receptor is said to be a receptor for such ligand(s). Generally, ligand-receptor binding induces one or more biological responses, such the recruitment of a downstream protein (e.g., a receptor interactor) to interact with the ligand-activated receptor. In some embodiments, a ligand and its target receptor are in different cells, such that one cellular reaction or response can be relayed to the next cell through ligand-receptor binding.

As used herein, the term "receptor interactor" refers to a protein that is induced or recruited to interact with a receptor after ligand activation of the receptor. The receptor interactor may bind to the ligand-activated receptor to affect its function or downstream signaling. In the present invention, the receptor interactor does not interact with the receptor prior to ligand activation. For example, ligand-activated G protein-coupled receptors (GPCRs) activate heterotrimeric G proteins. In order to turn off this response, the activated GPCRs need to be desensitized. During the desensitization process, GPCRs are first phosphorylated by G protein-coupled receptor kinases (GRKs). After GRK phosphorylation of the GPCRs, arrestin binds to the GPCRs to block further G protein-mediated signaling. In this example, arrestin is the receptor interactor of GPCR. Their interaction is induced by ligand activation of GPCR.

As used herein, the term "cleavage sequence" refers to an amino acid sequence that is recognized and cleaved, i.e., through hydrolysis of the peptide backbone, by a specific protease. The specificity of a protease relies largely on the protease recognition of the cleavage sequence.

As used herein, the term "protease" refers to an enzyme capable of breaking down proteins into smaller polypeptides or amino acids by the hydrolysis of the peptide backbone. Proteases have evolved many times and different classes of proteases can perform the same reaction by completely different catalytic mechanisms. Some proteases hydrolyze the peptide backbone only when they recognize a specific amino acid sequence, i.e., a cleavage sequence, present in a protein or polypeptide. Some proteases hydrolyze the peptide backbone regardless of the amino acid sequence of the protein.

As used herein, the term "effector" refers to a molecule that can modulate the activity of another molecule, e.g., a protein or gene, thus affecting the subsequent cellular response. In some embodiments, the effector may be a transcription factor, which can affect gene expression. An effector (e.g., transcription factor) can either activate or inhibit gene expression. An effector (e.g., transcription factor) can recognize and bind to a specific nucleic acid sequence, e.g., an effector-responsive element (e.g., a promoter element or a repressor element), that is often located upstream of a nucleic acid sequence encoding a reporter/modifier gene, to activate or inhibit gene expression. The binding of the effector (e.g., transcription factor) to the transcription factor-responsive element may recruit other proteins to help enhance or block downstream gene expression. In the present invention, the terms "effector" and "transcription factor" may be used interchangeably.

As used herein, the term "receptor fusion polypeptide" refers to a fusion of a receptor, a cleavage sequence, and an effector joined in tandem series by way of linkers. In the present invention, the receptor fusion polypeptide is expressed in all or a subset of cells (e.g., in the second-order cell in a cellular circuit). The receptor interacts with the tethered ligand in the first-order cell in the cellular circuit.

As used herein, the term "protease fusion polypeptide" refers to a fusion of a receptor interactor and a protease joined in tandem series by way of a linker.

As used herein, the term "reporter/modifier gene" refers to a gene that has the ability to generate a signal. In some embodiments, the signal is a detectable signal. The detectable signal may be a physiological signal, a chemical or biochemical molecule, or a fluorescent signal. In other embodiments, the signal is the decrease or even removal of a previous signal that was present before the reporter gene is expressed. The expression of the reporter/modifier gene is often under the control of a regulatory element, e.g., an effector-responsive element (e.g., a promoter element or a repressor element).

As used herein, the term "linker" refers to a linkage between two elements, e.g., protein domains. A linker can be a covalent bond or a spacer. The term "bond" refers to a chemical bond, e.g., an amide bond or a disulfide bond, or any kind of bond created from a chemical reaction, e.g., chemical conjugation. The term "spacer" refers to a moiety (e.g., a polyethylene glycol (PEG) polymer) or an amino acid sequence of a certain length occurring between two polypeptides or polypeptide domains to provide space and/or flexibility between the two polypeptides or polypeptide domains. An amino acid spacer is part of the primary sequence of a polypeptide (e.g., joined to the spaced polypeptides or polypeptide domains via the polypeptide backbone).

As used herein, the term "joined" is used to describe the combination or attachment of two or more elements, components, or protein domains by means including chemical conjugation, recombinant means, and chemical bonds, e.g., disulfide bonds and amide bonds. For example, two single peptides can be joined to form one contiguous protein or polypeptide structure through chemical conjugation, a chemical bond, a peptide linker, or any other means of covalent linkage. In some embodiments, a membrane-targeting domain is joined to a tethered ligand by way of a peptide linker, wherein the N-terminus of the peptide linker is joined to the C-terminus of the membrane-targeting domain through a chemical bond, e.g., a peptide bond, and the C-terminus of the peptide linker is joined to the N-terminus of the tethered ligand through a chemical bond, e.g., a peptide bond.

As used herein, the term "tandem series" refers to the arrangement of proteins or peptides in which the amino acids encoding one protein or peptide is placed after those encoding another protein or peptide in a single polypeptide.

As used herein, the term "polypeptide" describes a single polymer in which the monomers are amino acid residues which are joined together through amide bonds. A polypeptide is intended to encompass any amino acid sequence, either naturally occurring, recombinant, or synthetically produced.

As used herein, the term "nucleic acid molecule" refers to polymers of nucleotides of any length, and includes DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A nucleic acid molecule may contain modified nucleotides, such as methylated nucleotides and their analogs. If present, modification to the nucleotide structure may be imparted before or after assembly of the polymer. The sequence of nucleotides may be interrupted by non-nucleotide components. A nucleic acid molecule may be further modified after synthesis, such as by conjugation with a label. Other types of modifications include, for example, substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the nucleic acid molecule(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Nucleic acid molecules can also contain analogous forms of ribose or deoxyribose sugars that are generally known in the art, including, for example, 2'-O-methyl-, 2'-O-allyl-, 2'-fluoro-, or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein the phosphate is replaced by P(O)S ("thioate"), P(S)S ("dithioate"), (O)NR$_2$ ("amidate"), P(O)R, P(O)OR', CO, or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl, or araldyl. Not all linkages in a nucleic acid molecule need to be identical. The preceding description applies to all nucleic acid molecules referred to herein, including DNA and RNA.

As used herein, the term "vector" refers to a nucleic acid molecule capable of transporting another nucleic acid molecule to which it has been linked. One type of vector is a "plasmid," which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids.

DETAILED DESCRIPTION OF THE INVENTION

The present invention features methods for labeling a cellular circuit (e.g., a neuronal circuit). The methods of the invention may be used to show how individual cells and complex cellular circuits connect and interact. The methods of the invention may be used to label cellular circuits in vivo or in vitro. In some embodiments, the methods of the invention may be used to label and trace cells located at different body parts of an organism, e.g., in a fly, mouse, or human. The methods of the invention may be used to label any cell-cell interaction, such as at the synapse, the neuromuscular junction, the apical or basal epithelium, gap junctions, tight junctions, and points of interaction between immune cells. For example, the methods of the invention may be used to label and manipulate cellular circuits in the nervous system, such as the olfactory and visual systems, the immune system, and other tissues.

I. Components of the System for Labeling and Manipulating Cellular Circuits

Figure 1:
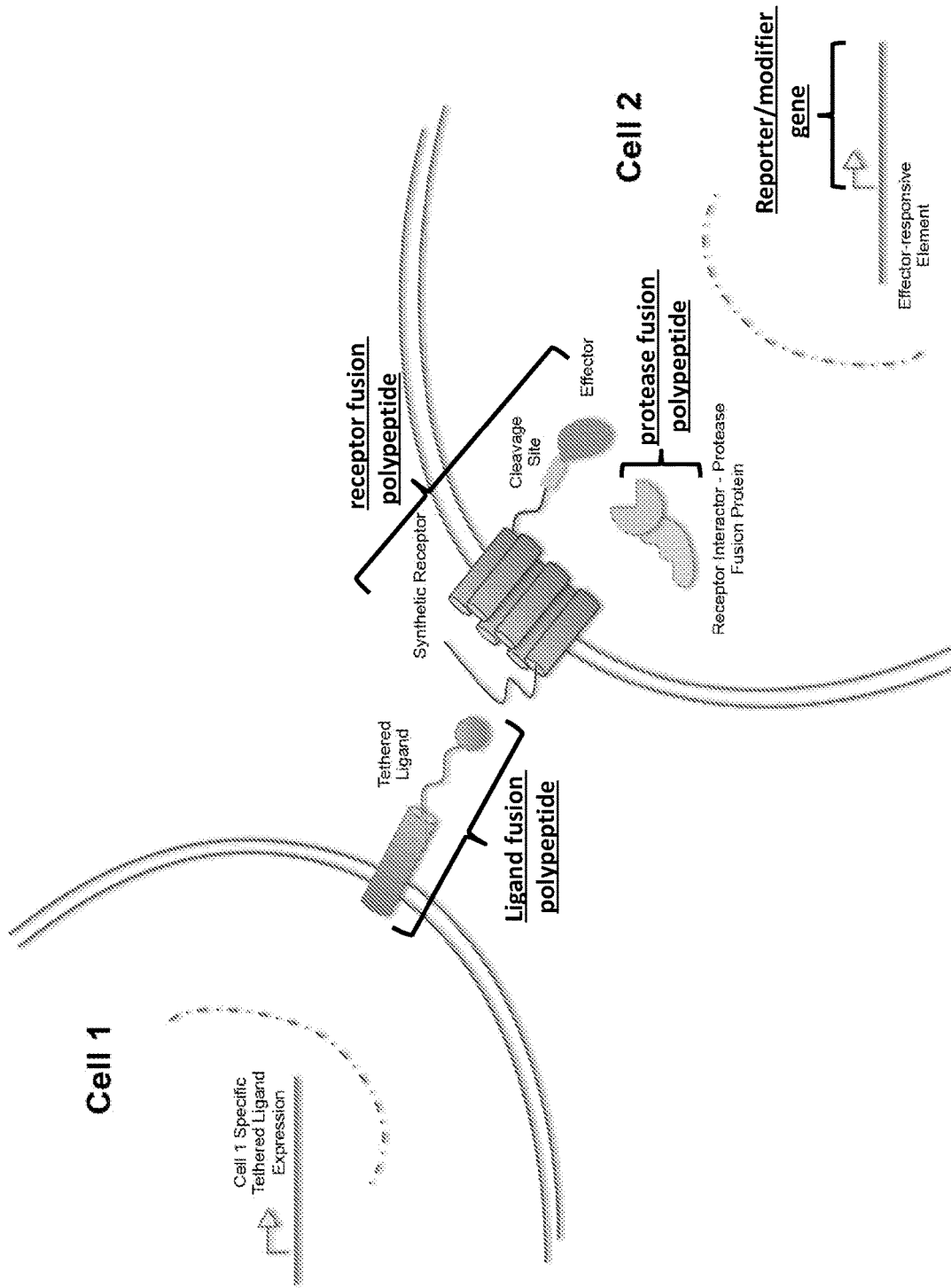
FIG. 1 is a schematic illustration of the system for labeling and manipulating cellular circuits described in this invention. A membrane tethered ligand (ligand fusion polypeptide) expressed by cell 1 interacts with the corresponding receptor (receptor fusion polypeptide) expressed by cell 2. Ligand-activation of the receptor recruits receptor interactor-protease fusion protein (protease fusion polypeptide) to the receptor. The protease cleaves the specific cleavage sequence/site and releases the effector. The effector translocates into the nucleus and initiates the transcription of the reporter/modifier gene.

The features of an embodiment of the invention are shown in FIG. 1. The first-order cell expressing a ligand fusion polypeptide is presumed to be in contact with a second-order cell. The second-order cell expresses a receptor fusion polypeptide and a protease fusion polypeptide. The ligand fusion polypeptide, receptor fusion polypeptide, and protease fusion polypeptide are described in detail herein. Upon ligand interaction and activation of the receptor in the second-order cell, the receptor recruits its receptor interactor (which is joined to a protease, forming the protease fusion polypeptide). Since receptor activation brings the protease in close proximity to the cleavage sequence/site linking the receptor and the effector, the protease cleaves at the cleavage sequence/site and releases the effector (e.g., a transcription factor) from the receptor fusion polypeptide. The released effector then enters the nucleus of the second-order cell to activate the expression of the reporter/modifier gene by binding to a specific effector-responsive element located upstream of the reporter/modifier gene. In some embodiments, depending on the nature and function of the effector, the released effector can exert its function in the cytoplasm. Each component of the system for labeling and manipulating cellular circuits is described in detail further herein.

In some embodiments of the invention, the ligand fusion polypeptide, receptor fusion polypeptide, and protease fusion polypeptide may be expressed in the same cell. If the ligand binds and interacts with (e.g., activates) the receptor, the receptor recruits its receptor interactor (which is joined to a protease, forming the protease fusion polypeptide). The protease in the protease fusion polypeptide cleaves at the cleavage sequence/site and releases the effector (e.g., a transcription factor) from the receptor fusion polypeptide. The released effector then enters the nucleus of the cell to activate the expression of the reporter/modifier gene by binding to a specific effector-responsive element located upstream of the reporter/modifier gene. Thus, to assay whether a potential ligand interacts with a receptor, a cell may be transfected with nucleic acid molecules each encoding the ligand fusion polypeptide, receptor fusion polypeptide, protease fusion polypeptide, and reporter/modifier gene. Expression of the reporter/modified gene may be measured (e.g., using fluorescence) to assay if the potential ligand interacts with the receptor.

II. Ligand Fusion Polypeptide

The first-order cell in a cellular circuit contains a tethered ligand that interacts with a receptor in a second-order cell. The first-order cell expresses a ligand fusion polypeptide, which contains a membrane-targeting domain and a tethered ligand joined in tandem series by way of a linker. In some embodiments, the ligand fusion polypeptide further includes an extracellular spacer domain between the membrane-targeting domain and the tethered ligand.

The membrane-targeting domain directs the ligand fusion polypeptide to the cell membrane of the first-order cell in a cellular circuit. In some embodiments, the membrane-targeting domain is the cytosolic and membrane regions of the protein Neurexin (NRX1), which directs the tethered ligand to the presynaptic area in neurons. NRX1 is a presynaptic, membrane protein with a single transmembrane domain. Other cytosolic, transmembrane, or extracellular regions of proteins may also be used to direct the ligand fusion polypeptide ubiquitously to the cell membrane of the first-order cell or to other areas of interest within the first-order cell. For example, to direct the ligand fusion polypeptide to the postsynaptic area in neurons, a dendrite-specific protein (e.g., Neuroligin) or the targeting portion thereof may be used as the membrane-targeting domain; to direct the ligand fusion polypeptide to tight junctions, a tight junction protein or the targeting portion thereof may be used as the membrane-targeting domain; to direct the ligand fusion polypeptide to a gap junction, a gap junction protein (e.g., a protein of the Connexin family) or the targeting portion thereof may be used as the membrane-targeting domain; to direct the ligand fusion polypeptide to the apical epithelium, an apical protein or the targeting portion thereof may be used as the membrane-targeting domain; and to direct the protein to the basal epithelium, a basal protein or the targeting portion thereof may be used as the membrane-targeting domain. In some embodiments, the membrane-targeting domain may be sensitive to an intracellular state or event, such as a change in intracellular ion concentrations, glucose levels, or action potentials. Thus, the membrane-targeting domain may conditionally control the localization of the ligand fusion polypeptide spatiotemporally in response to the state or event within the cell. For example, the ligand may be localized at the neuronal synapse only during periods of neuronal activity or at the cellular epithelium only during spikes or dips in glucose levels. Depending on the cellular circuit and the organism of interest, the membrane-targeting domains of different origins may be used. For example, human NRX1 may be used to target the ligand fusion polypeptide in a mammalian cell (e.g., a neuron in a neuronal circuit). In other embodiments, *Drosophila melanogaster* NRX1 may be used to target the ligand fusion polypeptide in a *Drosophila* cell (e.g., a *Drosophila* neuron in a neuronal circuit).

The tethered ligand may be joined to the membrane-targeting domain and faces the outside of the cell. For example, in the case of a neuronal circuit, the tethered ligand expressed in the first-order neuron faces the outside of the neuron, i.e., towards the synaptic cleft. The nature of the ligand may be different depending on the receptor in the second-order cell of the cellular circuit. In some embodiments, the tethered ligand is a ligand to a G protein-coupled receptor (GPCR). In some embodiments, the tethered ligand is a peptide or non-peptide ligand. In some embodiments, the ligand is a designed synthetic ligand, which signals a GPCR or GPCR-like protein. In some embodiments, the ligand is a designed synthetic analog of a peptide, which signals a GPCR or GPCR-like protein. In some embodiments, the ligand is a designed synthetic ligand, which signals a GPCR or GPCR-like protein. In some embodiments, the tethered ligand is selected from a group consisting of a human glucagon peptide, a glucose-dependent insulinotropic polypeptide (GIP), a glucagon-like peptide-1 (GLP1), a motilin peptide (MLN), a vasopressin, an oxytocin, a Bursicon, a ligand to an odorant receptor, a ligand to a visual receptor, a ligand to a β2-adrenergic receptor (ADRB2), a ligand to an arginine vasopressin receptor 2 (AVPR2), a ligand to an oxytocin receptor, a ligand to a serotonin receptor 1a (HTR1A), a ligand to a m2 muscarinic acetylcholine receptor (CHRM2), a ligand to a chemokine (C-C motif) receptor 5 (CCR5), a ligand to a dopamine D2 receptor (DRD2), a ligand to a kappa opioid receptor (OPRK), a ligand to an α1a-adregenic receptor (ADRA1A), and an analog thereof. In certain embodiments, the tethered ligand is a human glucagon peptide, which is an agonist of the human glucagon receptor. In certain embodiments, the tethered ligand is an analog of human glucagon peptide, which is an agonist of the human glucagon receptor. A signal peptide from mammalian trypsin may be fused to the human glucagon peptide. The signal peptide from trypsin directs the ligand fusion polypeptide to the endoplasmic reticulum of the first-order cell, which is necessary for its expression on the cell membrane. Many alternative signal peptides, besides the trypsin signal peptide, could be used. Other ligands or synthetic signaling factors may be used as long as they interact with the receptor in the second-order cell. The ligand-receptor pair may include, but is not limited to, G protein-coupled receptors (GPCRs) and the ligands that bind them, and any designed or synthetic ligand-receptor pair in which a receptor protein mediates a cellular signal in response to a ligand. Other types receptors include receptor tyrosine kinases, steroid hormone receptors, and protease-activated receptors. The ligand may also include a non-peptide ligand that may be covalently attached to a protein sequence expressed in the first-order cell of a cellular circuit through a protein moiety such as, but not limited to, a tetra-cysteine sequence.

In some embodiments, the ligand fusion polypeptide may further contain an extracellular spacer domain between the membrane-targeting domain and the tethered ligand. The extracellular spacer domain serves to extend the tethered ligand across the space between two cells in a cellular circuit and position the tethered ligand at the appropriate location to interact with the receptor in the second-order cell. In certain embodiments, the extracellular spacer domain is the extracellular domain of a human intercellular adhesion molecule 1 (ICAM1) or a splice variant thereof. A splice variant of the extracellular domain of ICAM1 may include a portion of the extracellular domain of ICAM1. The extracellular domain of ICAM1 or a splice variant thereof may be joined by way of a linker to the membrane-targeting domain, e.g., NRX1, such that the extracellular domain of ICAM1 or a splice variant thereof resides in the synaptic space. The large size of the extracellular domain of ICAM1 or a splice variant thereof approximately spans the length of the synaptic space. In the context of trans-synaptic cellular communication, the extracellular domain of ICAM1 or a splice variant thereof is appropriately sized to extend the tethered ligand through the synaptic space, though other extracellular domains of proteins could be used alone or fused in combination with each other to achieve an appropriate extracellular spacer domain which spans the synaptic space or any desired distance between cells.

In some embodiments, the extracellular spacer domain may be derived from endogenous or heterologous proteins. The extracellular spacer domains may have different lengths, flexibility, and posttranslational modifications. In some embodiments, the extracellular spacer domain may be sensitive to the extracellular environment to provide conditional logic for the presentation of the ligand. In one example, a "split" or destabilized extracellular spacer domain, such as split-GFP, may be used to prevent proper presentation of the ligand, unless the ligand is in the presence of the complementary spacer domain, which would then reconstitute the full extracellular spacer domain and properly display the ligand. In another example, a ligand-receptor pairing may be used in which the presence of two distinct ligands is required to target a single receptor. In another example, two ligand-receptor pairings may be used in which the presence of two distinct ligands and two receptors is required to target a single common cell. Each ligand would be expressed under different regulatory control regions in order to achieve signaling only in the union of their regulated gene expression patterns. In some embodiments, the signal might be restricted to a subset of cells genetically or randomly through means of mosaicism.

In other embodiments, a tethered ligand may be encoded by a genetically encoded recombinant polymer, which may include one or more unnatural molecules, e.g., unnatural amino acids.

A vector containing a DNA construct encoding a ligand fusion polypeptide may be constructed using conventional molecular cloning techniques. Different vectors may be used for their expressions in various cellular circuits and organisms of interest. In some embodiments, a mammalian expression vector may be used for expression of the ligand fusion polypeptide in mammalian cells. Vectors suitable for expression in mammalian systems are well-known in the art, such as pcDNA3.1, pCMV, and pCAGGS. One of skill in the art would be able to choose the appropriate expression vectors for the desired system. The DNA construct encoding a ligand fusion polypeptide may be placed under a regulatory sequence which controls expression of the gene. A mammalian Kozak sequence may be placed at the beginning of the coding sequence to denote the site of translation initiation and to increase the rate of translation. Other regulatory sequences and mediators of gene transcription and translation could be used to direct the expression and expression level of the tethered ligand. One of skill in the art is generally familiar with regulatory sequences and mediators that may be used to regulator gene expression in mammalian cells. In some embodiments, a consensus intronic sequence and a synthetic 21 nucleotide A-T rich sequence may be placed at the 5' untranslated region (UTR) of the gene. In some embodiments, a viral p10 polyadenylation sequence may be used to replace a SV40 polyadenylation sequence at the 3' UTR. In some embodiments, other polyadenylation sequences may be used. In some embodiments, sequences such as the Woodchuck Hepatitis Virus (WHP) Posttranscriptional Regulatory Element (WPRE) sequence may be used immediately 5' to the polyadenylation sequence to increase expression of genes delivered by viral vectors. These modifications help to increase stability of the transcribed mRNA.

In other embodiments, in addition to a mammalian system, a vector may be used for expression of the ligand fusion polypeptide in other organisms, e.g., Drosophila. An example of such a vector is shown in SEQ ID NO: 1. The construct in the example given here is in a pUASTattB vector. This construct is placed under the control of the regulatory sequence UAS (upstream activating sequence), such that the tethered ligand construct would not be expressed except in the presence of the Gal4 transcription factor. The construct contains a Drosophila Kozak sequence. Following the Drosophila Kozak sequence, the sequence encodes the human glucagon peptide, which is a ligand to the glucagon receptor. The human glucagon peptide is joined to the extracellular domain of ICAM1, which serves as the extracellular spacer domain, through a linker sequence. Finally, the extracellular domain of ICAM1 is followed by the sequence encoding the transmembrane domain of NRX1.

III. Receptor Fusion Polypeptide

The second-order cell in a cellular circuit contains a receptor that can be activated by the tethered ligand in the first-order cell. In the present invention, the second-order cell is transfected with three nucleic acid molecules. The first nucleic acid molecule encodes a receptor fusion polypeptide that contains a receptor, a cleavage sequence, and an effector. The second nucleic acid molecule encodes a protease fusion polypeptide that contains a receptor interactor and a protease. In some embodiments, the third nucleic acid molecule encodes a reporter/modifier gene under the control of an effector-responsive element. In other embodiments, the third nucleic acid molecule encodes a protein that the effector may bind to. The expression of the reporter/modifier gene is activated by binding of the effector to the effector-responsive element that is located upstream of the reporter/modifier gene.

The receptor fusion polypeptide contains a receptor, a cleavage sequence, and an effector joined in tandem series by way of linkers. The receptor may be a transmembrane receptor, such as G protein-coupled receptors (GPCRs). In some embodiments, the GPCR is a human GPCR. Transmembrane receptors include, but are not limited to, human glucagon receptor (GCGR), glucose-dependent insulinotropic polypeptide receptor (GIPR), glucagon-like peptide-1 receptor (GLPR), motilin peptide receptor (MLNR), receptor for Bursicon, odorant receptor, visual receptor, β2-adrenergic receptor (ADRB2), arginine vasopressin receptor 2 (AVPR2), oxytocin receptor, serotonin receptor 1a (HTR1 A), m2 muscarinic acetylcholine receptor (CHRM2), chemokine (C-C motif) receptor 5 (CCR5), dopamine D2 receptor (DRD2), kappa opioid receptor (OPRK), or α1a-adregenic receptor (ADRA1A). In some embodiments, the receptor is the receptor of a designed synthetic ligand-receptor pair in which a receptor protein mediates a cellular signal in response to a ligand. Other classes of transmembrane receptors include, but are not limited to, receptor tyrosine kinases (RTKs), such as IGF1R, epidermal growth factor receptor (EGFR), ErbB2/HER2/Neu or related RTKs, receptor serine/threonine kinases, such as Transforming Growth Factor-beta (TGFβ), activin, or Bone Morphogenetic Protein (BMP) receptors, cytokine receptors, such as receptors for the interferon family for interleukin, erythropoietin, granulocyte colony-stimulating factor (G-CSF), and granulocyte macrophage colony-stimulating factor (GM-CSF), and tumor necrosis factor (TNF) and leptin receptors, as well as other receptors, which are not necessarily membrane bound, such as estrogen receptor 1 (ESR1), and estrogen receptor 2 (ESR2).

In some embodiments, the nucleotide sequence encoding the receptor is modified to increase interaction of the receptor with its receptor interactor (described in detail herein). The modification may include replacing all or part of the nucleotide sequence of the C-terminal region of the receptor with a nucleotide sequence which encodes an amino acid sequence which has higher affinity for the receptor interactor than the original sequence. For example, the C-terminal region of the receptor may be replaced by a nucleotide sequence encoding all or a part of the C-terminal region of an AVPR2, an angiotensin receptor-like 1 (AGTRL1), a gastrin-releasing peptide receptor (GRPR), an F2PL1, a chemokine (C-X-C motif) receptor (CXCR2/IL-8B), or a chemokine (C-C motif) receptor 4 (CCR4).

In some embodiments, the nucleotide sequence encoding the receptor is modified to mutate downstream signaling. For example, a GPCR (e.g., a GCGR, a GIPR, a GLPR, a MLNR, a receptor for Bursicon, an odorant receptor, a visual receptor, an ADRB2, an AVPR2, an oxytocin receptor, a HTR1A, a CHRM2, a CCR5, a DRD2, a OPRK, and an ADRA1A) may be modified to disrupt downstream signaling. In some embodiments, the nucleotide sequence encoding the GPCR or a part thereof is modified to increase or decrease interaction of the GPCR with the receptor interactor. In some embodiments, the nucleotide sequence encoding an intracellular loop of the GPCR is modified. In certain embodiments, the modification includes replacing part of the nucleotide sequence of the second intracellular loop (between the third and fourth transmembrane regions) of a GPCR with a nucleotide sequence that encodes an amino acid sequence that mutates downstream signaling of the receptor. For example, modifying an intracellular loop (e.g., the second intracellular loop between the third and fourth transmembrane regions) of a GPCR may change the interaction between an activated GPCR and its receptor interactor (e.g., β-arrestin). In some embodiments, modifying the intracellular of the GPCR may increase the affinity between an activated GPCR and its receptor interactor. In other embodiments, modifying the loop may decrease the affinity between an activated GPCR and its receptor interactor. The cleavage sequence between the receptor and the effector in the receptor fusion polypeptide refers to an amino acid sequence that can be recognized and cleaved by certain proteases. In the present invention, the tethered ligand in the first-order cell interacts with the receptor in the second-order cell. The activated receptor protein then recruits the receptor interactor which is joined to the protease in the protease fusion polypeptide (described in detail further herein). Once the protease is in proximity to the cleavage sequence, it recognizes and cleaves, i.e., through hydrolysis of the peptide backbone, the cleavage sequence. The amino acid sequence of a cleavage sequence depends on the type of protease used in the protease fusion polypeptide. Any cleavage sequence can be used that is specifically recognized by a cognate protease. Examples of protease and cleavage sequence pairs include, but are not limited to, the tobacco etch virus nuclear inclusion A (TEV) protease and its cleavage sequence E-$X_{aa}$-$X_{aa}$-Y-$X_{aa}$-Q-(G/S) (e.g., ENLYFQS (SEQ ID No: 33)), and the nonstructural protein 3 protease domain of the hepatitis C virus (NS3 HCV) and its cleavage sequence DEMEECSQ (SEQ ID NO: 36). The kinetics of the cleavage reaction may be adjusted by mutating the amino acid sequence of the cleavage sequence or the amino acid sequence of the protease active site. Additionally, the protease used may also be responsive to a chemical that may be introduced to inhibit or activate the protease to varying degrees, therefore modulating the kinetics of the cleavage reaction or providing a temporal window in which the protease may be active.

The effector in the receptor fusion polypeptide refers to a molecule that binds to a protein or a nucleic acid sequence and regulates protein activity or gene expression. An effector may recognize and bind to a specific nucleic acid sequence, such as an effector-responsive element (e.g., a promoter element or a repressor element) that is usually located upstream of a nucleic acid sequence encoding a gene of interest. In some embodiments, the effector molecule is a transcription factor. As conventionally known in the art, a transcription factor is a molecule that is involved in gene regulation and transcription. A transcription factor can either activate or inhibit gene transcription. Transcription factors may perform this function alone or with other proteins in a complex. In some embodiments when a transcription factor activates gene transcription (also called a transcription activator), the binding of the transcription factor to the promoter element may recruit other proteins to help enhance downstream gene transcription. In other embodiments when a transcription factor represses or inhibits gene transcription (also called a transcription repressor), the binding of the transcription factor to the repressor element may inhibit gene transcription by, for example, blocking accjyess of the RNA polymerase to the gene. Transcription factors are typically classified according to the structure of their DNA-binding domain, which are generally (a) zinc fingers, (b) helix-turn-helix, (c) leucine zipper, (d) helix-loop-helix, or (e) high mobility groups. The Rel/Nuclear Factor kB (NF-kB) and Activating Protein-1 (AP-1) are among the most studied transcription factor families. They have been identified as important components of signal transduction pathways leading to pathological outcomes such as inflammation and tumorigenesis. Other transcription factors and their families include cAMP response element-binding protein (CREB), heat shock/E2F family, POU family, Fos family (e.g., cFos), and ATF family. Some synthetic transcription factors include LexA, tetracycline controlled transcription factor (tTA), tTA2, Gal4, LexA, and QF. In certain embodiments of the invention, the effector is tTA, tTA2, Gal4, LexA, or QF. The transcription factor Gal4 binds to the regulatory element UAS. The transcription factor QF binds to the regulatory element QUAS. In some embodiments of the present invention, once the cleavage sequence is cleaved by the protease in the protease fusion polypeptide, the transcription factor is freed and relocates to the nucleus to activate transcription and expression of the reporter gene in the second-order cell of a cellular circuit.

In some embodiments, the effector molecule may be an epigenetic modifying enzyme (e.g., a methyl transferase), a site-specific recombinase (e.g., Cre, Dre, Flp, or PhiC31), a transposase (e.g., a transposase that binds to the P-element), an endonuclease enzyme (e.g., CRISPR associated protein 9 (Cas9)), or any other protein that enables genome targeting and/or editing. In other embodiments, the effector may interact with other proteins, such as components in an endogenous signaling pathway.

In some embodiments, the receptor fusion polypeptide may additionally include protein domains that direct the membrane localization of the receptor to locations of interest within the cell, to provide greater specificity in the ligand-receptor interaction between the first- and second-order cells in the cellular circuit, and/or to increase the amount of receptor present at the cell-cell contact site. For example, to localize the receptor fusion polypeptide at the neuronal synapse, a localization domain, such as the cytosolic domain of the postsynaptic protein Neuroligin may be joined to the N- or C-terminus of the receptor in the receptor fusion polypeptide. If the localization domain is between the receptor and the effector molecule, or if the localization domain is after the effector molecule, additional cleavage sequence may be inserted between the localization domain and the effector to ensure that the effector is fully freed upon receptor activation and protease cleavage.

A vector containing a DNA construct encoding a receptor fusion polypeptide may be constructed using conventional molecular cloning techniques. Different vectors may be used for their expressions in various cellular circuits and organisms of interest. In some embodiments, a mammalian expression vector may be used for expression of the receptor fusion polypeptide in mammalian cells. Vectors suitable for expression in mammalian systems are well-known in the art, such as pcDNA3.1, pCMV, and pCAGGS. The DNA construct may contain a fusion of the human glucagon receptor, GCGR, a TEV protease cleavage sequence (TEV sequence), and an effector (e.g., a transcription factor, e.g., QF). The construct may be further placed under the controls of enhancers and promoters to aid in initiating and activating transcription of the gene in mammalian cells. Examples of such enhancers and promoters are well-known in the art and include, but are not limited to, CAG, CMV, Ef1α, Thy1.2, and hSyn. A wide variety of regulatory regions could be used to express the receptor in desired subsets of cells. The 5' and 3' UTR sequences can also be varied to regulate the level of translation of the receptor fusion polypeptide. The concept for a fusion of a G-protein coupled receptor, a TEV sequence, and a transcription factor in tandem series has been described in, e.g., Barnea at al., *Proc. Natl. Acad. Sci. U.S.A.* 105:64-69, 2008. Upon receptor activation by its human glucagon peptide ligand, ArrTEV (described below) is recruited to the C-terminus of the glucagon receptor. The protease TEV proteolytically cleaves the TEV sequence, releasing the transcription factor QF, which can modulate gene transcription in the nucleus. While the glucagon receptor GCGR, the TEV sequence, and the transcription factor QF are described in this example of the receptor fusion polypeptide, all three components of the polypeptide could be switched to other receptors, cleavage sequences, and effectors, which are described above.

In other embodiments, a vector may be used for expression of the receptor fusion polypeptide in other organisms, e.g., *Drosophila*. An example of such a vector is shown in SEQ ID NO: 2. The DNA construct consists of a fusion of the human glucagon receptor, GCGR, a TEV protease cleavage sequence (TEV sequence), and the transcription factor QF. The construct is placed under the regulatory control of the *Drosophila* n-syb enhancer and the *Drosophila* synthetic core promoter (DSCP) sequence. The *Drosophila* Kozak sequence is placed following the DSCP sequence to initiate translation. Following the GCGR-TEV sequences-QF coding region, at the 3' UTR, the hsp70 polyadenylation sequence is used to terminate transcription.

IV. Protease Fusion Polypeptide

The protease fusion polypeptide in the second-order cell of a cellular circuit contains a receptor interactor and a protease, which are joined in tandem series by way of a linker. A receptor interactor refers to a protein that gets recruited to the membrane of the second-order cell and interacts with the receptor after receptor activation by the tethered ligand in the first-order cell. The nature of the receptor interactor is different depending on the receptor. In the case of GPCRs (e.g., a human glucagon receptor (GCGR)), the receptor interactor may be a protein from the arrestin family, e.g., β-arrestin or a kinase, e.g., Bark. The protease β-arrestin binds to the cytoplasmic face (e.g., the C-terminus and/or an intracellular loop (e.g., the second intracellular loop between the third and fourth transmembrane regions)) of an activated GPCR. In the case of RTKs, such as the EGFR, the receptor interactor may consist of a SH2 (Src homology domain 2) containing protein or fragment thereof, such as phospholipase C gamma (PLC-γ) or Src homology 2 domain containing transforming protein 1 (SHC1). In the case of receptor serine/threonine kinases, such as TGFβ, activin, and BMP receptors, the receptor interactor may be a Smad protein or fragment thereof. In the case of cytokine receptors, such as interferon-α/β or interferon-γ gamma receptors, the receptor interactor may be a signal transducer and activator of transcription (STAT) protein such as, but not being limited to, Stat1, Stat2; Janus kinase (JAK) proteins Jak1, Jak2, or Tyk2; or fragments thereof. In certain embodiments of the invention when the receptor is a GPCR (e.g., a glucagon receptor), the receptor interactor is an arrestin (e.g., β-arrestin).

The second component in the protease fusion polypeptide is a protease. Proteases are well characterized enzymes that cleave substrate proteins or peptides by proteolysis at a particular cleavage sequence. Some examples of proteases that may be used in the present invention include, but are not limited to, tobacco etch virus nuclear inclusion A (TEV) protease and the nonstructural protein 3 protease domain of the hepatitis C virus (NS3 HCV). In certain embodiments of the invention, the protease used in the system for labeling and manipulating cellular circuits is the TEV protease.

Different classes of protease recognize different cleavage sequences and can perform the same reaction by completely different catalytic mechanisms. Members of one family, the Ser/Thr proteases, cleave at serine and threonine residues. Other proteases include cysteine or thiol proteases, aspartic proteases, metalloproteinases, aminopeptidases, di- and tri-peptidases, carboxypeptidases, and peptidyl peptidases. Some proteases would bind to a single amino acid on the substrate protein and thus, would only have specificity for that residue. For example, trypsin protease cleaves at the carboxyl terminus of amino acid lysine or arginine. Some proteases are highly specific and only cleave substrate proteins at specific cleavage sites. The specific cleavage sequence recognized by a protease often contains a certain amino acid sequence that includes, e.g., 2-50 amino acids. In some embodiments, the peptide encoding a cleavage sequence may be isolated for experimental use. In certain embodiments of the invention, the protease is TEV protease, whose cleavage sequence is $E-X_{aa}-X_{aa}-Y-X_{aa}-Q-(G/S)$ (e.g., ENLYFQS (SEQ ID NO: 33)).

A vector containing a DNA construct encoding a protease fusion polypeptide may be constructed using conventional molecular cloning techniques. Different vectors may be used for their expressions in various cellular circuits and organisms of interest. In some embodiments, a mammalian expression vector may be used for expression of the receptor fusion polypeptide in mammalian cells. Vectors suitable for expression in mammalian systems are well-known in the art, such as pcDNA3.1, pCMV, and pCAGGS. The DNA construct may contain a fusion of the human β-Arrestin and the TEV protease (ArrTEV). The mammalian Kozak sequence may be placed immediately 5' to the coding sequence of ArrTEV to direct translation initiation. Many different regulatory regions could be used to direct the ArrTEV gene expression in mammalian cells. These include, but are not limited to, ubiquitous promoters, pan-neuronal promoters such as Thy1.2, hSyn, and Syn, and more specific promoters that target genetically defined subsets of cells, such as Cha, Gad, vGlut, Nkcc2, or any gene segment with regulatory activity.

In other embodiments, a vector may be used for expression of the protease fusion polypeptide in other organisms, e.g., *Drosophila*. An example of such a vector is shown in SEQ ID NO: 3. This construct is in a pUASTattB vector. The *Drosophila* Kozak sequence is placed immediately 5' to the coding sequence of ArrTev to direct translation initiation. The sequence of ArrTEV is placed under the elav promoter, a 5' gene fragment from the *Drosophila* elav gene, which directs expression pan-neuronally and neuron-specifically. In other versions of the system, the ArrTEV coding sequence may be placed under the control of an n-syb enhancer and a DSCP sequence, which is a stronger pan-neuronal and neuron-specific driver. The SV40 polyadenylation sequence is placed at the 3' end of the ArrTEV gene.

V. Reporter/Modifier Gene

As described previously, the second-order cell in a cellular circuit is transfected with three nucleic acid molecules. The first and second nucleic acid molecules encode the receptor fusion polypeptide and the protease fusion polypeptide, respectively. The third nucleic acid molecule encodes a reporter/modifier gene under the control of an effector-responsive element. The expression of the reporter gene is induced by binding of the effector (e.g., a transcription factor) to the effector-responsive element that is located upstream of the reporter/modifier gene.

In some embodiments, the reporter gene encodes the reporter protein that has the ability to generate a signal. In some embodiments, the signal is a detectable signal. The detectable signal may be a physiological signal, a chemical or biochemical molecule, or a fluorescent signal. For example, the reporter protein may be a florescent protein (e.g., a GFP or mtdTomato), which generates a fluorescent signal that can be detected using a fluorescence microscopy. Fluorescent proteins are well-known in the art, see, e.g., Giepmans et al., *Science* 312:217-224, 2006; Shaner et al., *Nat Methods* 2:905-909, 2005; and Zhang et al., *Nat Rev Mol Cell Biol.* 3:906-918, 2002.

In other embodiments, the signal may be the decrease or even removal of a previous signal that was present before the reporter protein is expressed. In some embodiments, the reporter/modifier protein may be a protein that blocks the signaling pathway which generates the previous signal. In other embodiments, the reporter protein may be a protein that induces cell death. In one example, the reporter protein may be a mutant of the shibire protein in *drosophila*. Temperature-sensitive mutations in shibire (shibire$^{ts}$) silence neuron firings at high temperatures (i.e., above 30° C.). Flies with the shibire$^{ts}$ gene can be raised at lower temperatures where their neurons will behave normally. The change in the behavior of the flies when they are put in a high temperature environment is often used to study the functions of specific neurons. In another example, the reporter protein may be a halorhodopsin, which is a light-gated ion pump that is often used in optogenetics to hyperpolarize (or inhibit), and thus silence specific excitable neurons. The expression of halorhodopsin inhibits specific neuron firings and thus, stops certain signal transductions. In yet another example, Kir2.1, an inward-rectifier potassium ion channel, can also be used to silence neuronal signaling.

Any DNA sequence that is responsive to the effector or the downstream signaling pathway initiated by the effector may be used to regulate the output of the system. Reporter/modifier genes include, but are not limited to, genes encoding endogenous proteins, fluorescent proteins (e.g., GFP), protein tags, proteins that mediate a change in cellular function (e.g., channelrhodopsins, mutant dynamin, ion channels, and metabolic enzymes), proteins that mediate a change in epigenetic state (e.g., methyl transferases and acetylases), proteins inducing cellular fate change (e.g., apoptotic proteins), proteins that mediate a change in endogenous cellular signaling (e.g., kinases), proteins that regulate the unfolded protein response, genome editing proteins that may modify portions of the genome, proteins that cause cell death, uracil phosphoribosyltransferase for the monitoring of gene expression, a luciferase protein, proteins that promote the growth or reproduction of a cell, proteins involved in the synthesis of a nucleotide, an amino acid, or a molecule (e.g., a cofactor) within a cell, proteins that confer resistance to a molecule (e.g., an antibiotic) that inhibits growth or reproduction of a cell, and many other types of genes. Multiple genes may be used as reporter/modifier genes whose expressions may be polycistronic or under distinct gene regulatory elements.

Additionally, the reporter/modifier gene in the second-order cell in the cellular circuit may encode a tethered ligand, either the same as the tethered ligand in the first-order cell or a different ligand, such that the expression of a tethered ligand would be an output of the system. This ligand may target the same receptor whose activation triggered the system output or a different receptor. Expressing the ligand as an output of the system can be used to trigger higher order or subsequent cell-cell interactions as mediated by the system described herein.

An example of a DNA construct encoding a reporter/modifier gene is shown in SEQ ID NO: 4. The reporter/modifier gene encodes the fluorescent protein mtdTomato, which is placed under the effector-responsive element QUAS. The transcription factor QF in the receptor fusion polypeptide (described previously), once released by cleavage of the cleavage sequence, binds to the effector-responsive element QUAS. At the 3' UTR, the hsp70 polyadenylation sequence is used to terminate transcription.

VI. Linker

In the present invention, a linker is used to describe a linkage or connection between polypeptides or protein domains. In some embodiments, a linker is a linkage between the membrane-targeting domain and the tethered ligand in the ligand fusion polypeptide, in which the membrane-targeting domain and the tethered ligand are joined in tandem series. In other embodiments, a linker is a linkage between the receptor and the cleavage sequence or between the cleavage sequence and the effector in the receptor fusion polypeptide, in which the receptor, the cleavage sequence, and the effector are joined in tandem series. In yet other embodiments, a linker is a linkage between the receptor interactor and the protease in the protease fusion polypeptide, in which the receptor interactor and the protease are joined in tandem series.

A linker can be a simple covalent bond, e.g., a peptide bond, a synthetic polymer, e.g., a polyethylene glycol (PEG) polymer, or any kind of bond created from a chemical reaction, e.g. chemical conjugation. In the case that a linker is a peptide bond, the carboxylic acid group at the C-terminus of one protein domain can react with the amino group at the N-terminus of another protein domain in a condensation reaction to form a peptide bond. Specifically, the peptide bond can be formed from synthetic means through a conventional organic chemistry reaction well-known in the art, or by natural production from a host cell, wherein a nucleic acid molecule encoding the DNA sequences of both proteins, e.g., a membrane-targeting domain and a tethered ligand, in tandem series can be directly transcribed and translated into a contiguous polypeptide encoding both proteins by the necessary molecular machineries, e.g., DNA polymerase and ribosome, in the host cell.

In the case that a linker is a synthetic polymer, e.g., a PEG polymer, the polymer can be functionalized with reactive chemical functional groups at each end to react with the terminal amino acids at the connecting ends of two proteins.

In the case that a linker (except peptide bond mentioned above) is made from a chemical reaction, chemical functional groups, e.g., amine, carboxylic acid, ester, azide, or other functional groups commonly used in the art, can be attached synthetically to the C-terminus of one protein and the N-terminus of another protein, respectively. The two functional groups can then react through synthetic chemistry means to form a chemical bond, thus connecting the two proteins together. Such chemical conjugation procedures are routine for those skilled in the art.

Spacers

In the present invention, a spacer can be a protein domain, such as ICAM1 or a splice variant thereof as described above, or a peptide spacer of varying lengths. Suitable peptide spacers that are known in the art include, for example, peptide linkers containing flexible amino acid residues such as glycine and serine. In certain embodiments, a spacer can contain peptide linker motifs, e.g., multiple or repeating motifs, of GS, GGS, GGG (SEQ ID NO: 6), GGGGS (SEQ ID NO: 7), GGSG (SEQ ID NO: 8), or SGGG (SEQ ID NO: 9). In certain embodiments, a spacer can contain 2 to 12 amino acids including motifs of GS, e.g., GS, GSGS (SEQ ID NO: 10), GSGSGS (SEQ ID NO: 11), GSGSGSGS (SEQ ID NO: 12), GSGSGSGSGS (SEQ ID NO: 13), or GSGSGSGSGSGS (SEQ ID NO: 14). In certain other embodiments, a spacer can contain 3 to 12 amino acids including motifs of GGS, e.g., GGS, GGSGGS (SEQ ID NO: 15), GGSGGSGGS (SEQ ID NO: 16), and GGSGGSGGSGGS (SEQ ID NO: 17). In yet other embodiments, a spacer can contain 4 to 12 amino acids including motifs of GGSG, e.g., GGSG (SEQ ID NO: 18), GGSGGGSG (SEQ ID NO: 19), or GGSGGGSGGGSG (SEQ ID NO: 20). In other embodiments, a spacer can contain motifs of GGGGS (SEQ ID NO: 21), e.g., GGGGSGGGGSGGGGS (SEQ ID NO: 22). In other embodiments, a spacer can also contain amino acids other than glycine and serine, e.g., multiple or repeating motifs of GN (e.g., GNGNGNGNGNGNGNGN (SEQ ID NO: 23)), GNGNGNGNGTG (SEQ ID NO: 24), GGGGAGGGG (SEQ ID NO: 25), GENLYFQSGG (SEQ ID NO: 26), SACYCELS (SEQ ID NO: 27), RSIAT (SEQ ID NO: 28), RPACKIPNDLKQKVMNH (SEQ ID NO: 29), GGSAGGSGSGSSGGSSGASGTGTAGGTGSGSGTGSG (SEQ ID NO: 30), AAANSSIDLISVPVDSR (SEQ ID NO: 31), or GGSGGGSEGGGSEGGGSEGGGSEGGGSEGGGSGGGS (SEQ ID NO: 32). The length of the peptide spacer and the amino acids used can be adjusted depending on the two protein domains involved and the degree of flexibility desired in the final protein construct. The length of the spacer can be adjusted to ensure proper protein folding and avoid aggregate formation. In certain embodiments of the invention, the linker contains the amino acid sequence GNGNGNGNGNGNGNGN (SEQ ID NO: 23) or GNGNGNGNGTG (SEQ ID NO: 24). It is understood that the spacer length will depend on the context that it is used, and that one of ordinary skill in the art will be able to ascertain the adequate length using standard techniques.

VII. Vectors and Regulatory Signals

The nucleic acids encoding the components of the system for labeling and manipulating cellular circuits may be included in nucleic acid vectors that can be delivered into the cells in a cellular circuit by conventional techniques known in the art (e.g., viral transduction, transfection, transformation, electroporation, calcium phosphate precipitation, direct microinjection, infection, etc). The choice of nucleic acid vectors depends in part on the type of cells in the cellular circuit and the organism of interest. The methods of labeling a cellular circuit described herein may be used in any tissue or cell type either in vitro or in vivo. The cells that may be labeled by the methods described herein include, but are not limited to, various cells in a mammalian system, such as neurons (e.g., olfactory receptor neurons, photoreceptor neurons, any type of neurons in the brain), epithelial cells, muscle cells, sensory cells, and cells that reside in various organs of the body, such as kidney cells, liver cells, and immune system cells. In some embodiments, the cells in a cellular circuit may be mammalian cells in culture. Examples of mammalian cell culture types include, but are not limited to, human embryonic kidney (HEK) (e.g., HEK293, HEK 293F), Chinese hamster ovary (CHO), HeLa, COS, PC3, Vero, MC3T3, NS0, Sp2/0, VERY, BHK, MDCK, W138, BT483, Hs578T, HTB2, BT20, T47D, NS0, CRL7O3O, and HsS78Bst cells. In additional to a mammalian system, the methods of labeling a cellular circuit described herein may be also used in other organism, e.g., *Drosophila*.

A nucleic acid sequence encoding the amino acid sequence of a component of the system for labeling and manipulating cellular circuits (e.g., the ligand fusion polypeptide, the receptor fusion polypeptide, the protease fusion polypeptide, or the reporter/modifier gene) may be prepared by a variety of methods known in the art. These methods include, but are not limited to, oligonucleotide-mediated (or site-directed) mutagenesis and PCR mutagenesis. A nucleic acid molecule encoding a component of the system for labeling and manipulating cellular circuits (e.g., the ligand fusion polypeptide, the receptor fusion polypeptide, the protease fusion polypeptide, or the reporter/modifier gene) may be obtained using standard techniques in molecular cloning, e.g., gene synthesis. Nucleic acid molecules can be synthesized using a nucleotide synthesizer or PCR techniques. Other standard cloning techniques may also be used to construct a nucleic acid sequence encoding the amino acid sequence of a component of the system for labeling and manipulating cellular circuits.

A nucleic acid sequence encoding a component of the system for labeling and manipulating cellular circuits (e.g., the ligand fusion polypeptide, the receptor fusion polypeptide, the protease fusion polypeptide, or the reporter/modifier gene) may be inserted into a vector capable of replicating and expressing the nucleic acid molecule in the cells of interest. Many vectors are available in the art. Examples of vectors include, but are not limited to, pcDNA3.1, pCMV, and pCAGGS. In certain embodiments of the invention, the vector used is pUASTattB. For example, many vectors may be used to transform eukaryotic host cells. It may be desirable to select vectors that have been modified for the specific purpose of expressing proteins in eukaryotic host cells. Expression systems have been designed for regulated and/or high level expression in such cells. For example, the insect cell/baculovirus system can produce a high level of protein expression of a heterologous nucleic acid segment, such as described in U.S. Pat. Nos. 5,871,986 and 4,879,236, both herein incorporated by reference, and which can be bought, for example, under the name MAXBAC® 2.0 from INVITROGEN® and BACKPACK™ BACULOVIRUS EXPRESSION SYSTEM FROM CLONTECH®. Other examples of expression systems include STRATAGENE'S COMPLETE CONTROL™ Inducible Mammalian Expression System, which involves a synthetic ecdysone-inducible receptor, or its pET Expression System, an *E. coli* expression system. Another example of an inducible expression system is available from INVITROGEN, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector and produce a nucleic acid sequence or its cognate polypeptide, protein, or peptide.

Each vector may contain various components that may be adjusted and optimized for compatibility with the particular cells of interest. For example, the vector components may include, but are not limited to, a regulatory element, an origin of replication, a selection marker gene, a multiple cloning site (MCS), a promoter (e.g., a TATA box), an enhancer, a ribosome binding site, a signal sequence, the nucleic acid sequence encoding protein of interest, and a transcription termination sequence. The type of vector and its components may be chosen and/or adjusted based on factors such as the target cell type and the level of expression desired. In some embodiments, different regulatory elements may be used to control expression of the components of the system for labeling and manipulating cellular circuits in different cell types. The nucleic acid sequence encoding protein of interest may include addition regulatory signals such as poly A sequences. One of skill in the art understands that it is important to employ a promoter or an enhancer that effectively directs the expression of the DNA construct in the organelle, cell type, tissue, organ, or organism chosen for expression. Those of skill in the art of molecular biology generally know the use of promoters, enhancers, and cell type combinations for protein expression (see, e.g., Sambrook, et al., Molecular Cloning: A Laboratory Manual (Fourth Edition), 2012). The promoters employed may be constitutive, tissue-specific, inducible, and/or useful under the appropriate conditions to direct high level expression of the introduced DNA construct, such as is advantageous in the large-scale production of recombinant proteins and/or peptides. The promoter may be heterologous or endogenous. Some examples of promoters and enhancers that help to regulate the initiation and activation of genes include CAG, CMV, Ef1α, Thy1.2, and hSyn. Other examples of promoters and enhancers include enhancers that are expressed in subsets of cells of interest, binary systems (UAS, QUAS, LexAOp, tetO), genomic locations such that knock-ins at these locations produce desired expression patterns, genomic fragments that are sufficient to drive expression in all or subsets of cells.

In some embodiments, internal ribosome entry sites (IRES) elements may be used to create multigene, or polycistronic, messages. IRES elements are able to bypass the ribosome scanning model of 5' methylated Cap dependent translation and begin translation at internal sites. IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message. In some embodiments, a multiple cloning site (MCS) may also be included in a vector. A MCS is a nucleic acid region that contains multiple restriction enzyme sites, any of which can be used in conjunction with standard recombinant technology to digest the vector.

The vectors or constructs of the present invention will generally include at least one termination signal. A "termination signal" or "terminator" includes a DNA sequence involved in specific termination of an RNA transcript by an RNA polymerase. In some embodiments, a terminator may be necessary in vivo to achieve desirable message levels. In eukaryotic systems, the terminator region may also include specific DNA sequences that permit site-specific cleavage of the new transcript so as to expose a polyadenylation site. This signals a specialized endogenous polymerase to add a stretch of about 200 adenosine residues (polyA) to the 3' end of the transcript. RNA molecules modified with this polyA tail appear to more stable and are translated more efficiently. The terminator and/or polyadenylation site elements can serve to enhance message levels and to minimize read through from the cassette into other sequences. Terminators contemplated for use in the invention include any known terminator of transcription described herein or known to one of ordinary skill in the art, including but not being limited to, for example, the termination sequences of genes, such as the bovine growth hormone terminator, viral termination sequences, such as the SV40 terminator. In some embodiments, the termination signal may be a lack of transcribable or translatable sequence, such as an untranslatable/untranscribable sequence due to a sequence truncation.

VIII. Visualization of the Cells in a Cellular Circuit

Fluorescent proteins may be used to visualize the labeled cells in a cellular circuit. In certain embodiments of the system for labeling and manipulating cellular circuits, the expression of the ligand fusion polypeptide is induced in the first-order cell by the presence of Gal4, and the resulting signaling in the second-order cell is mediated by the transcription factor QF. In order to visualize and differentiate the cells producing Gal4, QF, or both, a first membrane-tagged fluorescent protein (e.g., a GFP (see, e.g., SEQ ID NO: 5)) under the control of the regulatory element UAS and a second membrane-tagged fluorescent protein (which is of a different color compared to that of the first membrane-tagged fluorescent protein, e.g., a mtdTomato) under the control of the regulatory element QUAS may be delivered into the first- and second-order cells in a cellular circuit, respectively. Since Gal4 binds to the regulatory element UAS and QF binds to the regulatory element QUAS, GFP expression would indicate successful Gal4 induction and that the ligand fusion polypeptide is expressed. Similarly, mtdTomato expression in the second-order cell would indicate successful QF release from the receptor fusion polypeptide. Thus, QF is free to bind to QUAS and induce downstream expression of the reporter/modifier gene. In other versions of the system for labeling and manipulating cellular circuits, other regulatory elements and their transcription factors may be used, such as the regulatory element LexAop and the transcription factor LexA. Each of FIGS. 2-5 contains a group of fluorescent images that show the labeled neurons in a neuronal circuit. In these labeling experiments, the first-order cell in the cellular circuit is a pre-synaptic neuron and the second-order cell is a post-synaptic neuron or another higher order neuron. FIGS. 2A-2C, 3A-3C, and 4A-4C demonstrate the labeling of neurons in the olfactory circuit and FIGS. 5A-5C demonstrate the labeling of the visual system in flies.

IX. Kits

Any of the compositions described herein may be included in a kit. The kits will include, e.g., containers for the vectors or cells of the present invention, and any additional agents that can be used in accordance with the present invention.

The kits may include suitably aliquoted compositions of the present invention. The components of the kits may be packaged either in aqueous media or in lyophilized form. The containers of the kits will generally include, e.g., at least one vial, test tube, flask, bottle, or syringe, into which a component may be placed and suitably aliquoted. Where there are more than one component in the kit, the kit also will generally contain a second, third or other additional container into which the additional components may be separately placed. However, various combinations of components may be included comprised in a container. The kits of the present invention also will typically include a means for containing reagent containers in close confinement for commercial sale. Such containers may include injection or blow-molded plastic containers into which the desired vials are retained.

When the components of the kit are provided in one and/or more liquid solutions, the liquid solution is an aqueous solution. In some embodiments, the aqueous solution is sterile. The components of the kit may also be provided as dried powder(s). When reagents and/or components are provided as a dry powder, the powder can be reconstituted by the addition of a suitable solvent (e.g., sterile water or serum). It is envisioned that the solvent may also be provided in another container.

X. Applications of the System for Labeling and Manipulating Cellular Circuits

Labeling Tissue Bordering a Tumor

Genes encoding the ligand fusion polypeptide, under a specific promoter that is relevant to particular tumors, could be placed into cells of a tumor. Genes encoding the receptor fusion polypeptide and the protease fusion polypeptide, each under a general promoter, and the reporter/modifier gene that mediates the system output could be placed into cells of the tissue surrounding the tumor. The system output, which would be triggered in the receptor-containing cells that are in proximity to the tumor cells, could be the expression of certain proteins which marks or labels a perimeter around the tumor. Thus, a shell of tissue surrounding the tumor could be labeled for resection of the tumor.

Labeling and Suppressing Tumor Metastasis

Genes encoding the ligand fusion polypeptide, under a general promoter, could be placed into cells in tissues bordering or near a tumor. Genes encoding the receptor fusion polypeptide and the protease fusion polypeptide, each under a tumor-specific promoter and/or a general promoter, and the reporter/modifier gene that mediates the system output could be placed into cells of the tumor. Upon contact with ligand-containing cells, system output would be triggered in tumor cells. The system output could be the expression of certain proteins which marks the tumor cells. The tumor cells may have spread to the ligand-containing tissue. The system output could also be the release of inflammatory cues or the expression of certain proteins that would reprogram the cells away from the tumor-state or kill the tumor cells.

Suppressing Tumors by Interaction with Immune Cells

Genes encoding the ligand fusion polypeptide, under a general promoter, could be placed into immune cells. Genes encoding the receptor fusion polypeptide and the protease fusion polypeptide, each under a tumor-specific promoter and/or a general promoter, and the reporter/modifier gene that mediates the system output could be placed into tumor cells. Activation of the system through contact between the immune cells and the tumor cells, could produce inflammatory proteins, reprogram the tumor cells, or induce cell death of the tumor cells.

Suppressing Autoimmune Diseases

Cellular targets of autoimmune diseases, such as pancreatic cells in patients with type 1 diabetes, could be given genes encoding the ligand fusion polypeptide under a general promoter. Some cells of the patient's immune system could be given the receptor fusion polypeptide and the protease fusion polypeptide, each under a general promoter, as well as the reporter/modifier gene that mediates the system output. Activation of the system through interaction between the immune cells and the cellular targets of an autoimmune disease, could lead to the expression of genes encoding proteins that down-regulate inflammation or cause the death of the immune cells.

Suppressing Epilepsy

Genes encoding the ligand fusion polypeptide could be placed into cells whose activity results in epilepsy. Genes encoding the receptor fusion polypeptide and the protease fusion polypeptide and the reporter/modifier gene that mediates the system output could be placed widely in the brain of an epileptic patient or specifically in certain areas of interest in the brain. With the ligand fusion polypeptide targeted to the pre-synapse, activation of the system could lead to system output in the postsynaptic partners of cells. System output could result in the death of these cells or in a silencing or down-regulation of their activity.

Alternatively, with the ligand fusion polypeptide targeted to the post-synaptic density and with the receptor fusion polypeptide and/or the protease fusion polypeptide targeted to inhibitory neurons, the system output could mediate a constitutive increase in activity of inhibitory neurons that directly provide input to ligand-expressing neurons in the epileptic locus, thus specifically silencing or damping their epileptic activity.

Tracing and Manipulating Neural Circuits

As previously described, the system can be used to trace and manipulate neural circuits, which can reveal valuable information about circuit structure and function. Labeled cells can also be used as targets for cell sorting. Gene expression of these cells could then be profiled and unique gene expression patterns could be identified.

Identifying Novel Ligands or Optimizing Existing Ligands

A system for identifying novel ligands or optimizing existing ligands for receptors of interest would include a host organism that expresses the receptor fusion polypeptide and the protease fusion polypeptide and contains the reporter/modifier gene that mediates the system output. The system output can either be measured in the cell (e.g. fluorescence) or contributes a fitness advantage to the host cell. A population of these host cells would then be transformed with a library encoding diverse potential ligands that are expressed as fusions with a tether that bind them to the host cell, thereby assaying receptor activation by each ligand variant in a cell-autonomous fashion. Ligands would be either completely random or mutated from an initial ligand to be optimized. Transformed host cells would each express a ligand variant. A ligand variant that activates the receptor would affect the level of reporter signal. In the case of a fluorescent or colorimetric reporter, cells containing ligands that activate receptors to a high level would be identified and isolated by colorimetry, fluorimetry, or fluorescence-activated cell sorting (FACS). In the case of a reporter that confers a selective advantage to host cells, the population of host cells would be grown to a high density, and the ligands conferring the selective advantage can be identified by sequencing the isolated nucleic acids from the population of cells in which the selective advantage has occurred versus the population of cells in which it has not. Ligands identified can then be further optimized through the generation of a mutant library.

EXAMPLES

Example 1—Labeling and Manipulating Cellular Circuits in Mammals

Transgenic mammals (e.g., mice) are generated by conventional methods, such as genome editing (e.g., by CRISPR/Cas9 technology) and viral transduction. For example, to label or manipulate neurons in a neuronal circuit in the brain of a transgenic mouse, the pre-synaptic neurons are expressing the ligand fusion polypeptide and the post-synaptic neurons are expressing the receptor fusion polypeptide, the protease fusion polypeptide, and the reporter/modifier gene. The brain, or parts thereof, of the transgenic mouse is fixed and stained by immunohistochemistry for visualization and subsequent analysis.

Example 2—Generation of Transgenic Flies

Lines of transgenic flies were generated by PhiC31 integrase mediated, site-directed genomic integration of constructs in attB-containing plasmids. The integrated constructs were genes encoding the ligand fusion polypeptide, the receptor fusion polypeptide, and the protease fusion polypeptide, and genes containing the reporter/effector genes. These constructs were respectively directed to attP40 and attP8, two different genomic landing sites which were generated and characterized previously (see, e.g., Markstein et al., *Nat. Gene.* 40:476-483, 2008).

Collecting numerous distinct genes into a single construct, which was then integrated into the *Drosphila* genome, facilitated the generation of transgenic *Drosophila* containing all components of the system for labeling and manipulating cellular circuits. Other means of generating transgenic organisms or cells containing the system components are known in the art (see, e.g., Groth et al., *Genetics* 166:1775-1782, 2004 and Markstein et al., *Nat. Gene.* 40:476-483, 2008).

Example 3—Labeling and Manipulating Cellular Circuits in *Drosophila*

Flies were raised according to standard methods known to those familiar with the art (see, e.g., Example 2). Flies were dissected to recover the central brain, which was then fixed and stained by immunohistochemistry, according to methods known to those familiar with the art.

Each of FIGS. 2-5 contains a group of fluorescent images that show the labeled neurons in a neuronal circuit. In these labeling experiments, the first-order cell in the cellular circuit is a pre-synaptic neuron and the second-order cell is a post-synaptic neuron or another higher order neuron. FIGS. 2A-2C, 3A-3C, and 4A-4C demonstrate the labeling of neurons in the olfactory circuit and FIGS. 5A-5C demonstrate the labeling of photoreceptor cells.

Figures 2A, 2B, 2C:
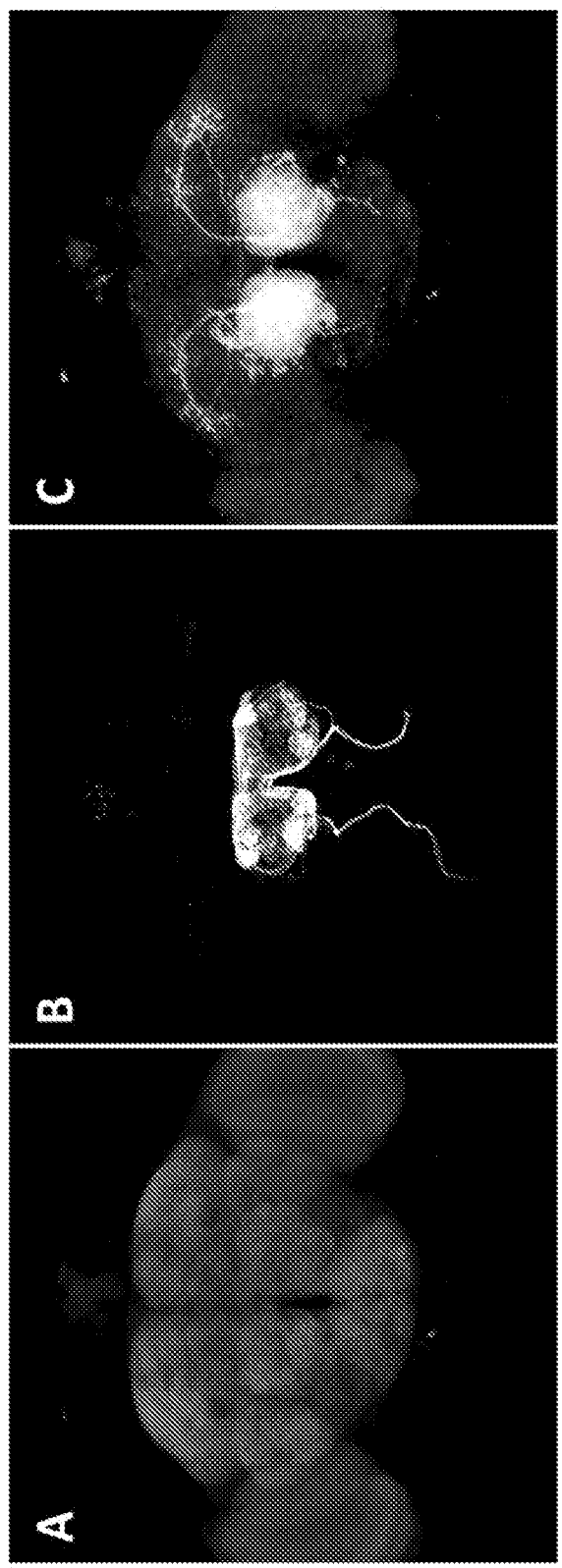
FIGS. 2A-2C are a group of images showing the tracing of projection neurons in the olfactory system of *D. melanogaster*. Collapsed Z-series of a brain from a transgenic fly in which OR83b-Gal4 drives the expression of tethered glucagon ligand and mCD8-GFP in the pre-synaptic olfactory receptor neurons (B). Binding of glucagon to the glucagon receptors on the post-synaptic neurons initiates mtdTomato expression and reveal the dendrites and axons of the post-synaptic projection neurons and local interneurons (C). Anti-NCad immunohistochemistry counterstains all neuropils (A), anti-GFP immunohistochemistry labels olfactory receptor neurons (B), and anti-HA immunohistochemistry reveals HA-tagged mtdTomato expression in local interneurons and projection neurons (C).
Figures 3A, 3B, 3C:
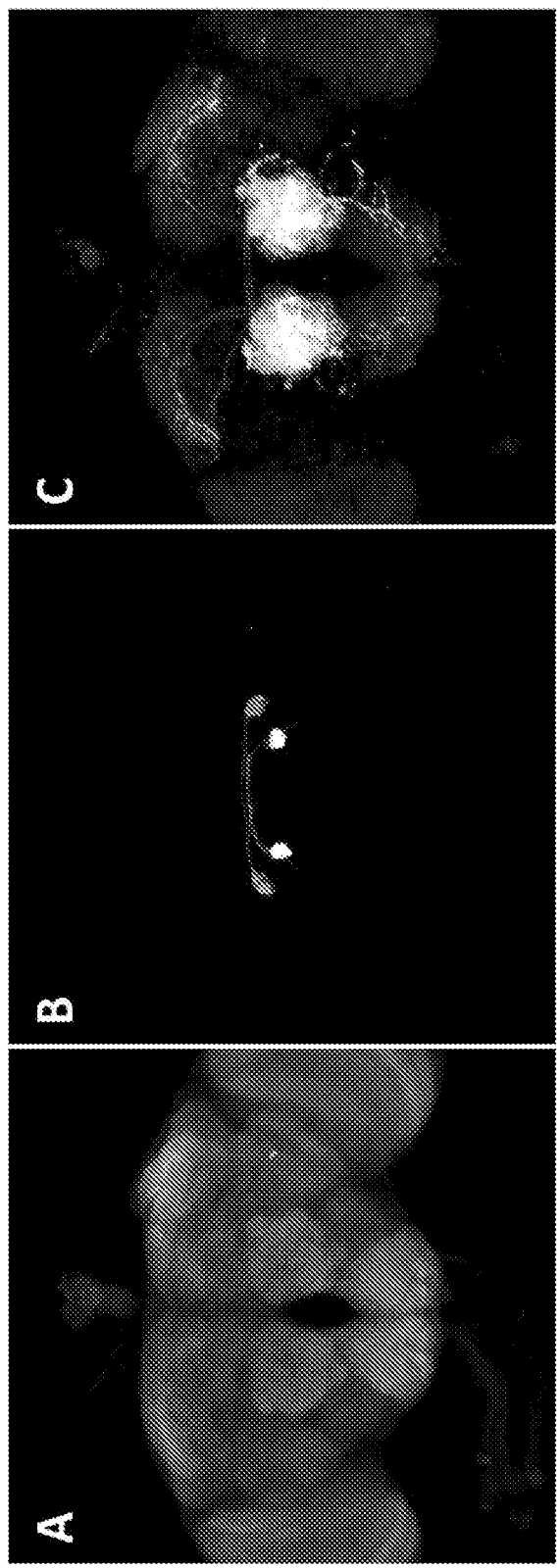
FIGS. 3A-3C are a group of images showing the tracing of post-synaptic neurons from expressing a particular olfactory receptor. Driver OR67d-Gal4 is used to drive the expression of tethered glucagon ligand and mCD8-GFP in the pre-synaptic neurons (B). Binding of glucagon to the glucagon receptors on the post-synaptic neurons initiates the expression of membrane-tagged Tomato in the post-synaptic neurons: projection neurons and antennal lobe local interneurons (C). Anti-NCad immunohistochemistry counterstains all neuropils (A), anti-GFP immunohistochemistry labels pre-synaptic olfactory receptor neurons (B), and anti-HA immunohistochemistry reveals HA-tagged mtdTomato expression in local interneurons and projection neurons (C). Optical sections through the brains were collapsed on the Z-axis to produce a single image.
Figures 4A, 4B, 4C:
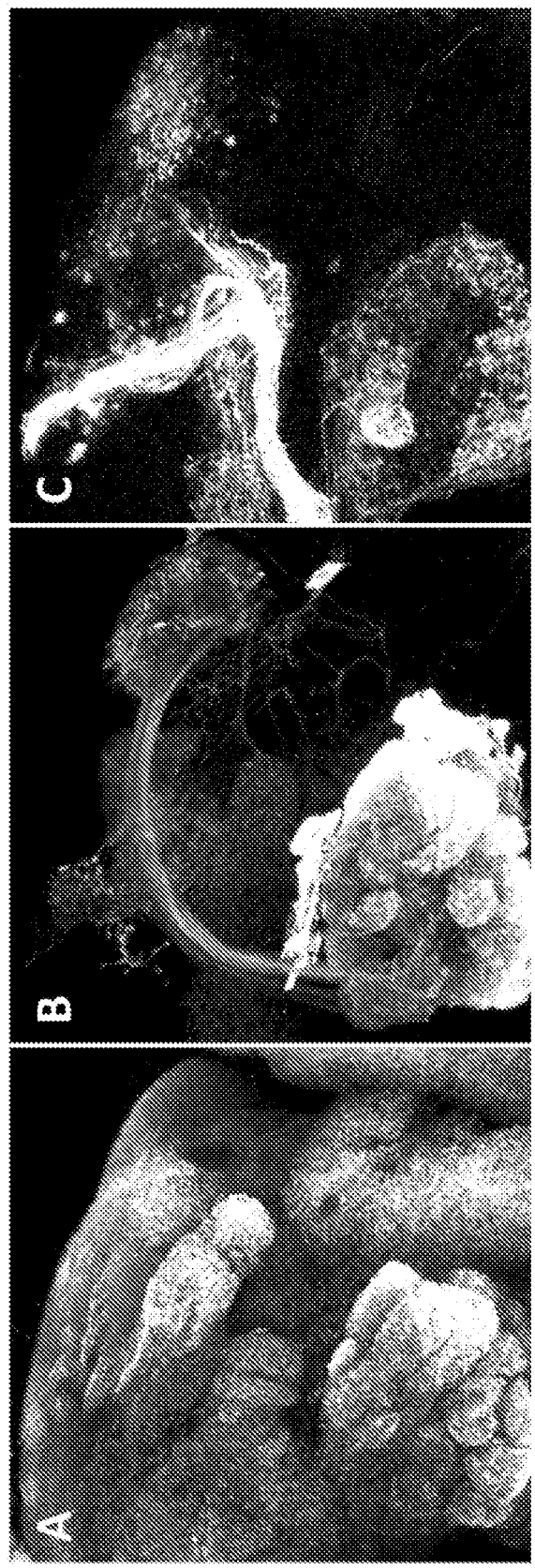
FIGS. 4A-4C are a group of images showing the tracing of higher order neurons in the olfactory circuit in *D. melanogaster*. Expressions of the tethered glucagon ligand and mCD8-GFP (B) in the projection neurons of the antennal lobe were induced by driver GH146-Gal4. Binding of glucagon to the glucagon receptors in the third-order neurons of the olfactory circuit initiates the Tomato expression (C). Anti-nc82 immunohistochemistry counterstains all neuropils (A) and projection neurons were detected using anti-GFP immunohistochemistry (B). Intrinsic membrane-tagged Tomato fluorescence reveals the post-synaptic signal (C). Optical sections through the brain were collapsed on the Z-axis to produce a single image.
Figures 5A, 5B, 5C:
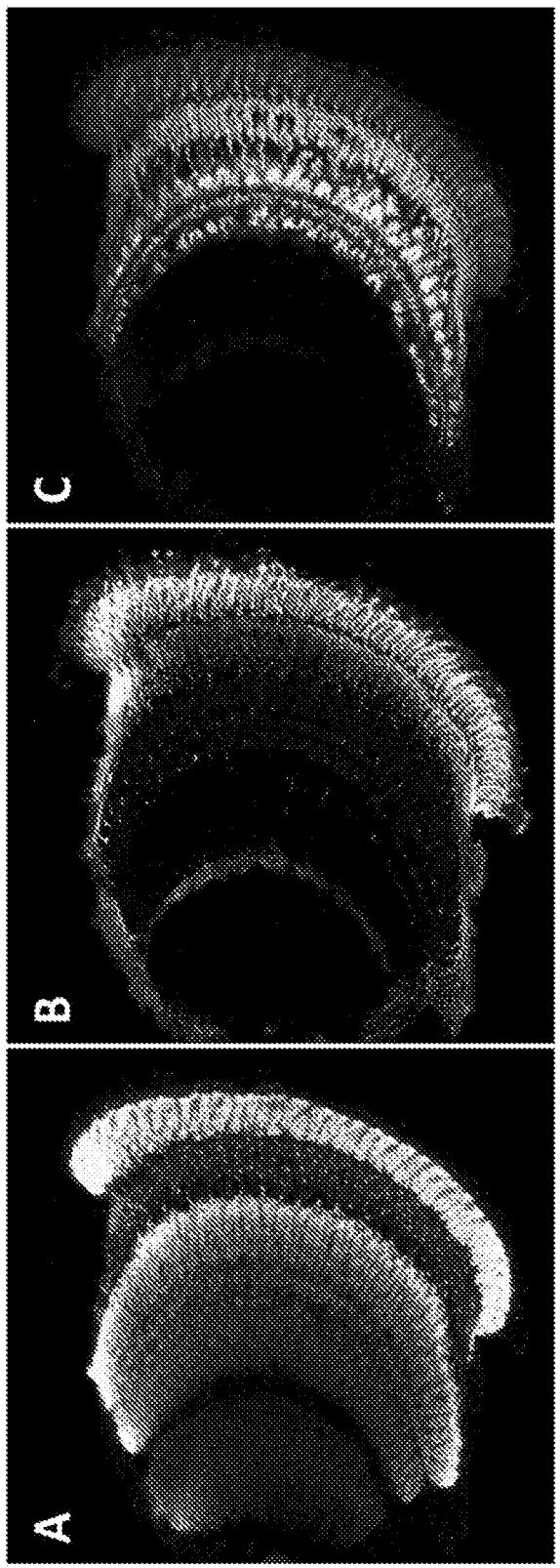
FIGS. 5A-5C are a group of images showing the tracing of projection from the retina in *D. melanogaster*. lGMR-Gal4, a driver known to be expressed in all photoreceptor cells, was used to induce tethered glucagon ligand and mCD8-GFP expressions (B). Binding of glucagon to the glucagon receptors in the post-synaptic neurons in the lamina and medulla initiates mtdTomato expression (C). Anti-nc82 immunohistochemistry counterstains all neuropils (A) and projection neurons were detected using anti-GFP immunohistochemistry (B). Intrinsic membrane-tagged Tomato fluorescence reveals the post-synaptic signal (C). Optical sections through the brain were collapsed on the Z-axis to produce a single image.

FIGS. 2A-2C show the expressions of tethered glucagon ligand and mCD8-GFP (which serves as a marker), both under the UAS control, driven by OR83b-Gal4 in the pre-synaptic olfactory receptor neurons and the expression of mtdTomato (which is the reporter/modifier gene) in the dendrites and axons of the post-synaptic projection neurons and local interneurons. FIGS. 3A-3C show the expressions of tethered glucagon ligand and mCD8-GFP driven by OR67d-Gal4 in the pre-synaptic neurons and the expression of mtdTomato in the projection neurons and antennal lobe local interneurons. Similarly, FIGS. 4A-4C show the expressions of tethered glucagon ligand and mCD8-GFP driven by GH146-Gal4 in the projection neurons of the antennal lobe and the expression of mtdTomato in the third-order neurons of the olfactory circuit. Finally, FIGS. 5A-5C show the expressions of tethered glucagon ligand and mCD8-GFP driven by IGMR-Gal4 in photoreceptor cells in the retina and the expression of mtdTomato in the post-synaptic neurons in the lamina and medulla.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents, and patent applications are herein incorporated by reference in their entirety to the same extent as if each individual publication, patent, or patent application was specifically and individually indicated to be incorporated by reference in its entirety.

Other embodiments are within the following claims.

What is claimed is:

1. A method of labeling a neuronal cellular circuit comprising two or more neuronal cells, wherein said method comprises:
   (a) transfecting a presynaptic neuronal cell with a first nucleic acid molecule encoding a ligand fusion polypeptide, wherein said ligand fusion polypeptide comprises a membrane-targeting domain and a tethered ligand joined by way of a linker, and
   (b) transfecting a postsynaptic neuronal cell or a higher-order neuron with:
      (i) a second nucleic acid molecule encoding a receptor fusion polypeptide, wherein said receptor fusion polypeptide comprises a receptor, a cleavage sequence, and an effector by way of linkers,
      (ii) a third nucleic acid molecule encoding a protease fusion polypeptide, wherein said protease fusion polypeptide comprises a receptor interactor and a protease by way of a linker, and
      (iii) a fourth nucleic acid molecule encoding a reporter/modifier gene under the control of an effector-responsive element,
   wherein said tethered ligand interacts with said receptor which induces said receptor interactor to interact with said receptor, wherein said protease cleaves said cleavage sequence to release said effector, and wherein the released effector binds to said effector-responsive element to induce the expression of said reporter/modifier gene in said postsynaptic neuronal cell or a higher-order neuron cell.

2. The method of claim 1, wherein said membrane-targeting domain is a membrane-bound protein or a fragment thereof.

3. The method of claim 1, wherein said tethered ligand is a ligand to a G protein-coupled receptor.

4. The method of claim 3, wherein said tethered ligand is a peptide or non-peptide ligand.

5. The method of claim 4, wherein said tethered ligand is selected from a group consisting of a human glucagon peptide, a glucose-dependent insulinotropic polypeptide, a glucagon-like peptide-1, a motilin peptide, a vasopressin, an oxytocin, a Bursicon, a ligand to an odorant receptor, a ligand to a visual receptor, a ligand to a β2-adrenergic receptor, a ligand to an arginine vasopressin receptor 2, a ligand to an oxytocin receptor, a ligand to a serotonin receptor 1a, a ligand to a m2 muscarinic acetylcholine receptor, a ligand to a chemokine (C-C motif) receptor 5, a ligand to a dopamine D2 receptor, a ligand to a kappa opioid receptor, a ligand to an ala-adrenergic receptor, and an analog thereof.

6. The method of claim 1, wherein said receptor is a transmembrane receptor.

7. The method of claim 6, wherein said transmembrane receptor is selected from a group consisting of a G protein-coupled receptor, a glucagon receptor, a glucose-dependent insulinotropic polypeptide receptor, a glucagon-like peptide-1 receptor, a motilin peptide receptor, a receptor for Bursicon, an odorant receptor, a visual receptor, a β2-adrenergic receptor, an arginine vasopressin receptor 2, an oxytocin receptor, a serotonin receptor 1a, a m2 muscarinic acetylcholine receptor, a chemokine (C-C motif) receptor 5, a dopamine D2 receptor, a kappa opioid receptor, and an ADRA1A.

8. The method of claim 1, wherein said cleavage sequence is ENLYFQS (SEQ ID NO: 33), ENLYFQY (SEQ ID NO: 34), ENLYFQL (SEQ ID NO: 35), or DEMEECSQ (SEQ ID NO: 36).

9. The method of claim 1, wherein said effector is a transcription factor.

10. The method of claim 1, wherein said receptor interactor is an inhibitory protein.

11. The method of claim 1, wherein said protease is tobacco etch virus nuclear inclusion A (TEV) protease or nonstructural protein 3 protease domain of the hepatitis C virus.

12. The method of claim 1, wherein the nucleotide sequence encoding said receptor is modified to increase interaction of said receptor with said receptor interactor.

13. The method of claim 12, wherein said modification comprises replacing all or part of the nucleotide sequence of the C-terminal region of said receptor with a nucleotide sequence which encodes an amino acid sequence which has higher affinity for said receptor interactor than the original sequence.

14. The method of claim 13, wherein the nucleotide sequence of a C-terminal region of said receptor is replaced by a nucleotide sequence encoding all or a part of the C-terminal region of an arginine vasopressin receptor 2, an angiotensin receptor-like 1, a gastrin-releasing peptide receptor, an F2PL1, a chemokine (C-X-C motif) receptor 2, or a chemokine (C-C motif) receptor 4.

15. The method of claim 1, wherein said reporter/modifier gene is an exogenous gene.

16. The method of claim 1, wherein said ligand fusion polypeptide further comprises an extracellular spacer domain between said membrane-targeting domain and said tethered ligand.

\* \* \* \* \*